United States Patent
Murray et al.

(10) Patent No.: US 11,298,242 B2
(45) Date of Patent: Apr. 12, 2022

(54) BIOMATERIAL DELIVERY DEVICE, AND RELATED SYSTEMS AND METHODS

(71) Applicant: Medos International Sarl, Le Locle (CH)

(72) Inventors: James Murray, Quincy, MA (US); John Riley Hawkins, Cumberland, RI (US); Benjamin Cleveland, Bellingham, MA (US); Alicia McDermott, Waltham, MA (US); Roman Lomeli, Plymouth, MA (US); John Dieselman, Providence, RI (US); Stephen Bornhoft, Raynham, MA (US); Christopher Ramsay, West Wareham, MA (US); Nicholas Pavento, North Attleboro, MA (US); Jan Klett, Aesch (CH); Stephane Gully, Rixheim (FR); Eric Buehlmann, Duxburry, MA (US); Thomas Gamache, Westport, MA (US); Roger Berger, Büren (CH)

(73) Assignee: Medos International Sarl

( * ) Notice: Subject to any disclaimer, the term of this patent is extended or adjusted under 35 U.S.C. 154(b) by 4 days.

(21) Appl. No.: 16/441,951

(22) Filed: Jun. 14, 2019

(65) Prior Publication Data
US 2020/0390566 A1    Dec. 17, 2020

(51) Int. Cl.
*A61F 2/46* (2006.01)
(52) U.S. Cl.
CPC .................................. *A61F 2/4601* (2013.01)

(58) Field of Classification Search
CPC .... A61F 2/4455; A61F 2/4601; A61F 2/4611; A61F 2/442; A61F 2/447; A61F 2/30767; A61F 2/4657; A61F 2310/00059; A61F 2310/00029; A61F 2310/00023; A61F 2310/00017; A61F 2310/00047;
(Continued)

(56) References Cited

U.S. PATENT DOCUMENTS 7,025,771 B2    4/2006    Kuslich et al.
7,153,306 B2    12/2006   Ralph et al.
(Continued)

FOREIGN PATENT DOCUMENTS

WO    2017/203234 A1    11/2017

*Primary Examiner* — Pedro Philogene
(74) *Attorney, Agent, or Firm* — BakerHostetler

(57) ABSTRACT

A system for delivering flowable biomaterial to an intervertebral disc space between adjacent vertebral bodies includes a delivery body defining a proximal end, a distal end spaced from the proximal end along a longitudinal direction, a cannulation extending from the proximal end to an opening adjacent the distal end, and a distal region including a tip that extends to the distal end. The distal region defines a maximum height at a location proximal of the distal end and measured along a second direction perpendicular to the longitudinal direction. The distal region is for indicating a distance between the adjacent vertebral bodies. The system includes a carrier having a longitudinaly elongate channel for carrying biomaterial and being insertable within the cannulation, as well as an advancement member configured for insertion within the cannulation to forcibly advance the biomaterial from the cannulation, through the opening, and into the disc space.

10 Claims, 25 Drawing Sheets

(58) Field of Classification Search
CPC ...... A61F 2002/469; A61F 2002/30904; A61F 2002/30593; A61F 2002/3071; A61F 2002/30785; A61F 2002/2835; A61F 2002/4693; A61F 2002/30601; A61F 2002/4694; A61F 2002/2817; A61F 2002/4627; A61F 2002/30153; A61B 17/8802; A61B 17/3742; A61B 17/3417; A61B 17/025; A61B 17/7094; A61B 17/8811; A61B 17/8833; A61B 2017/0256

See application file for complete search history.

(56) References Cited

U.S. PATENT DOCUMENTS

| | | |
|---|---|---|
| 7,294,132 B2 | 11/2007 | Raskin et al. |
| 7,306,611 B2 | 12/2007 | Cirotteau et al. |
| 7,316,689 B2 | 1/2008 | Lieberman |
| 7,544,196 B2 | 6/2009 | Bagga et al. |
| 7,763,025 B2 | 7/2010 | Ainsworth |
| 7,927,339 B2 | 4/2011 | Ralph et al. |
| 7,967,827 B2 | 6/2011 | Osorio et al. |
| 8,092,480 B2 | 1/2012 | Layne et al. |
| 8,317,865 B2 | 11/2012 | Osorio et al. |
| 9,351,739 B2 | 5/2016 | Mahoney et al. |
| 9,393,057 B2 | 7/2016 | MacMillan et al. |
| 9,456,830 B2 | 10/2016 | Greenhalgh |
| 9,610,110 B2 | 4/2017 | Truckai et al. |
| 9,668,881 B1 * | 6/2017 | Greenhalgh ........... A61B 90/57 |
| 9,681,900 B2 | 6/2017 | Fernyhough |
| 9,713,534 B2 | 7/2017 | Druma |
| 9,730,773 B2 | 8/2017 | Uchitel et al. |
| 2004/0024409 A1 * | 2/2004 | Sand ................... A61B 17/8819 606/92 |
| 2007/0043373 A1 | 2/2007 | Sala et al. |
| 2007/0043376 A1 | 2/2007 | Leatherbury et al. |
| 2008/0091207 A1 | 4/2008 | Truckai et al. |
| 2009/0149878 A1 | 6/2009 | Truckai et al. |
| 2010/0198140 A1 | 8/2010 | Lawson |
| 2011/0183287 A1 | 7/2011 | Lee |
| 2011/0308665 A1 | 12/2011 | McKay |
| 2012/0065694 A1 | 3/2012 | Simonson |
| 2012/0136442 A1 * | 5/2012 | Kleiner ................. A61F 2/4455 623/17.11 |
| 2012/0232658 A1 | 9/2012 | Morgenstern et al. |
| 2012/0316513 A1 | 12/2012 | Sharkey et al. |
| 2014/0257489 A1 | 9/2014 | Warren et al. |
| 2015/0112352 A1 | 4/2015 | Krause et al. |
| 2016/0089197 A1 | 3/2016 | Baroud |
| 2016/0106462 A1 | 4/2016 | McGillicuddy |
| 2016/0228261 A1 | 8/2016 | Emery et al. |
| 2017/0056084 A1 | 3/2017 | Linderman et al. |
| 2017/0164978 A1 | 6/2017 | Dean |
| 2017/0238984 A1 | 8/2017 | Kleiner |
| 2018/0008253 A1 | 1/2018 | Thommen et al. |

* cited by examiner

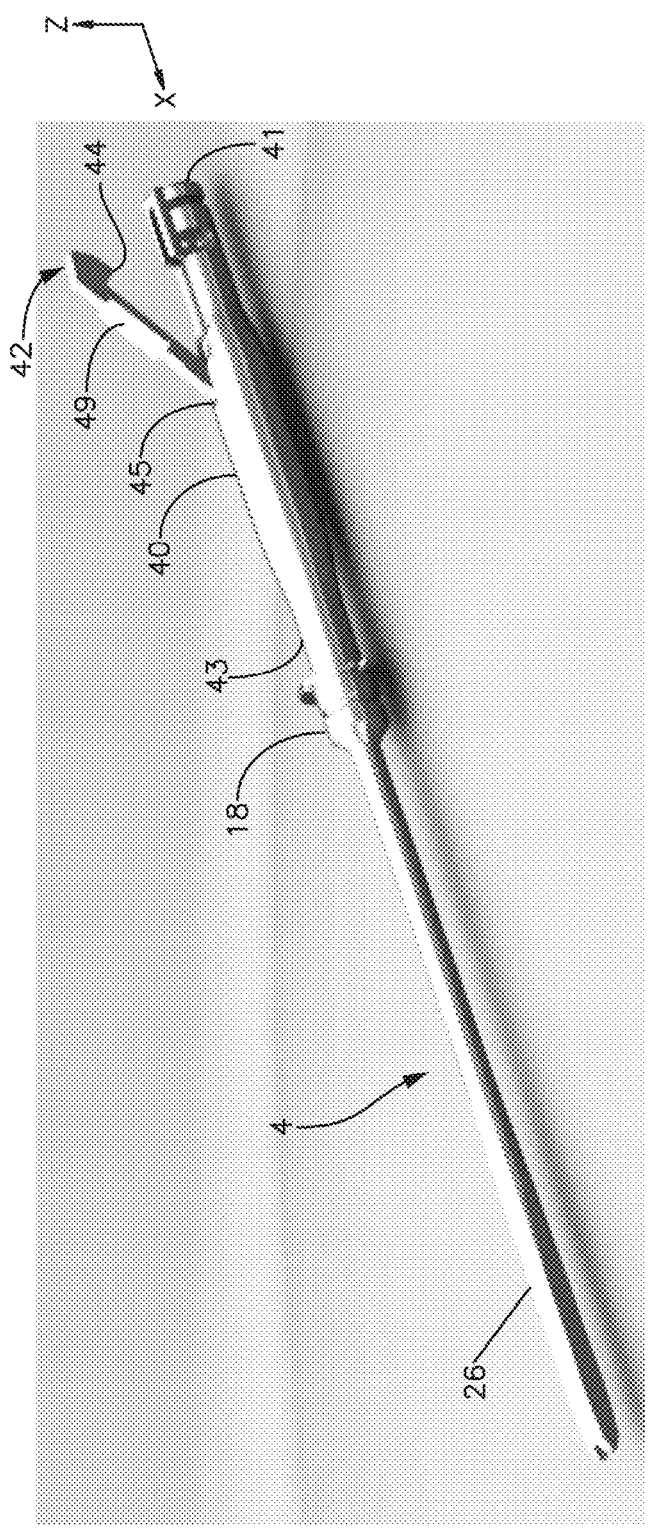
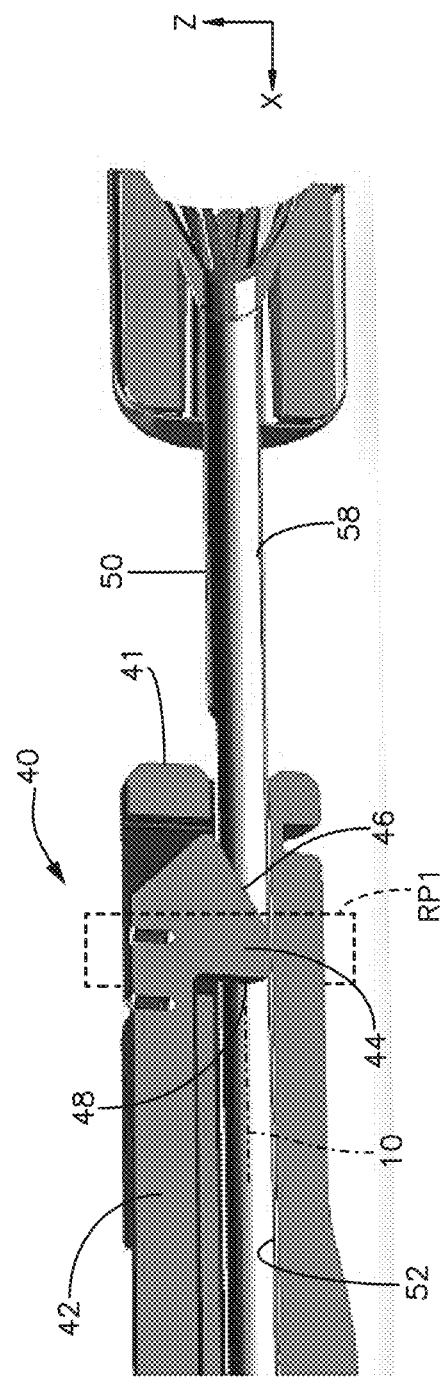
Fig.6A
Fig.6B

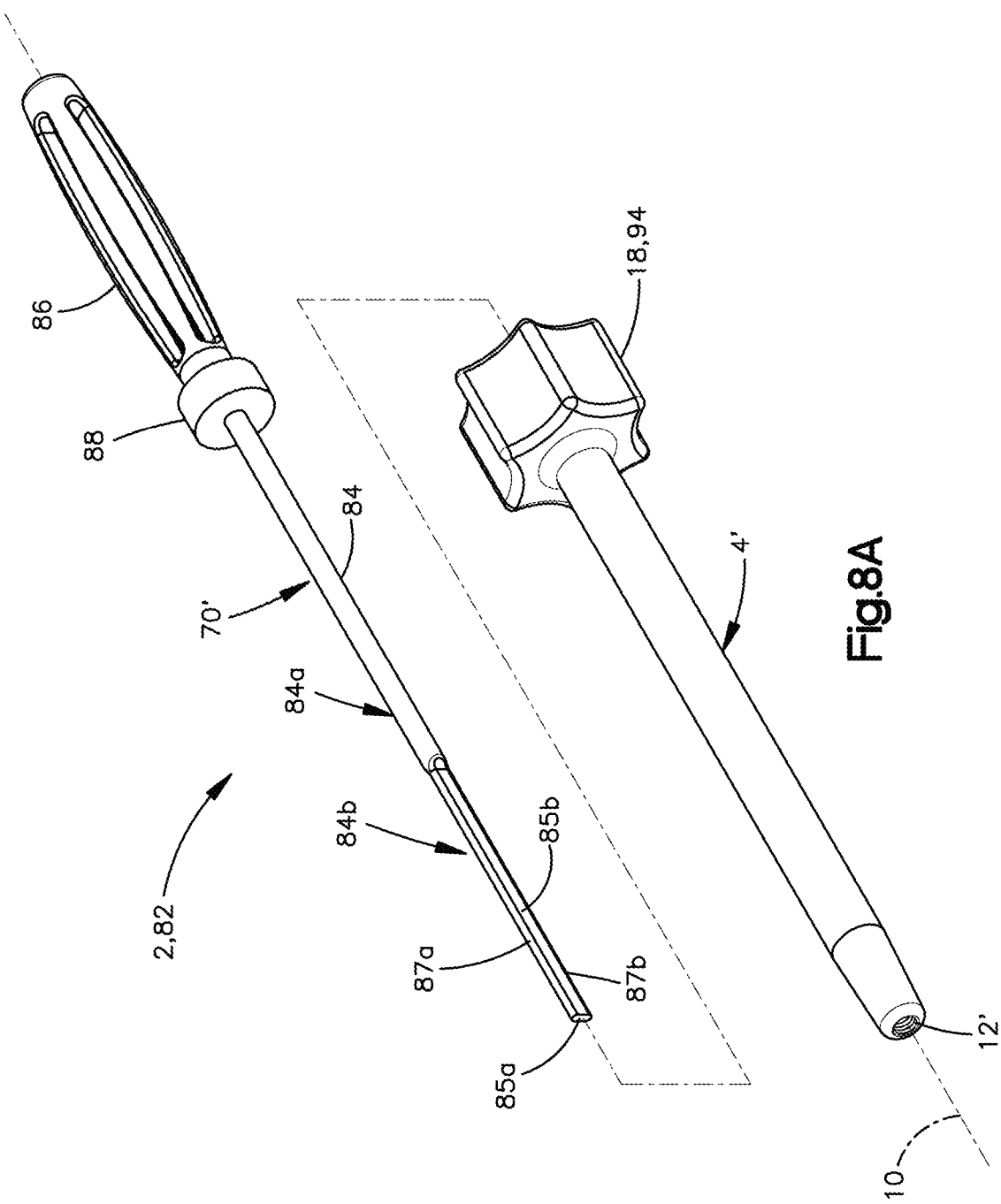

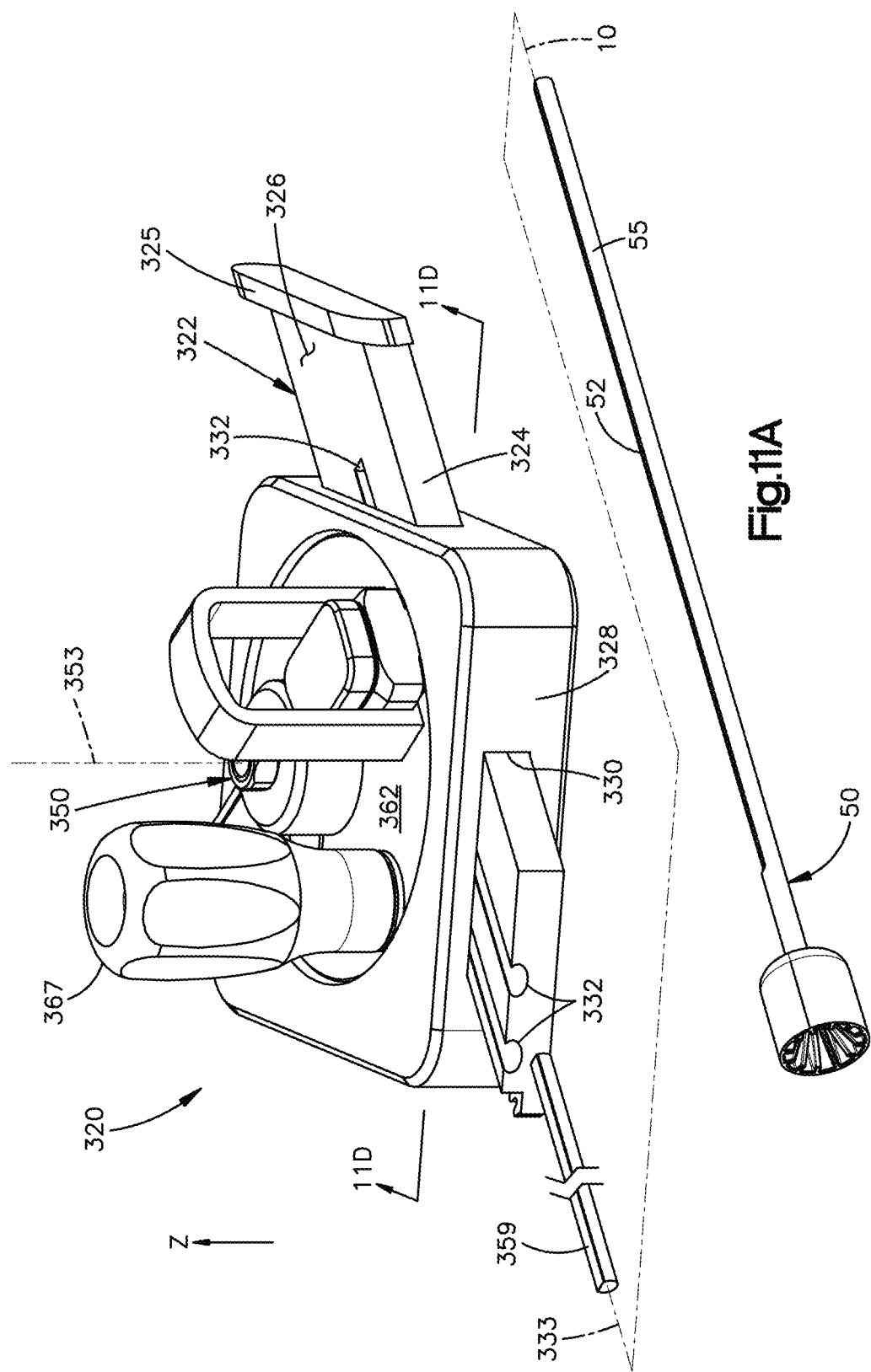

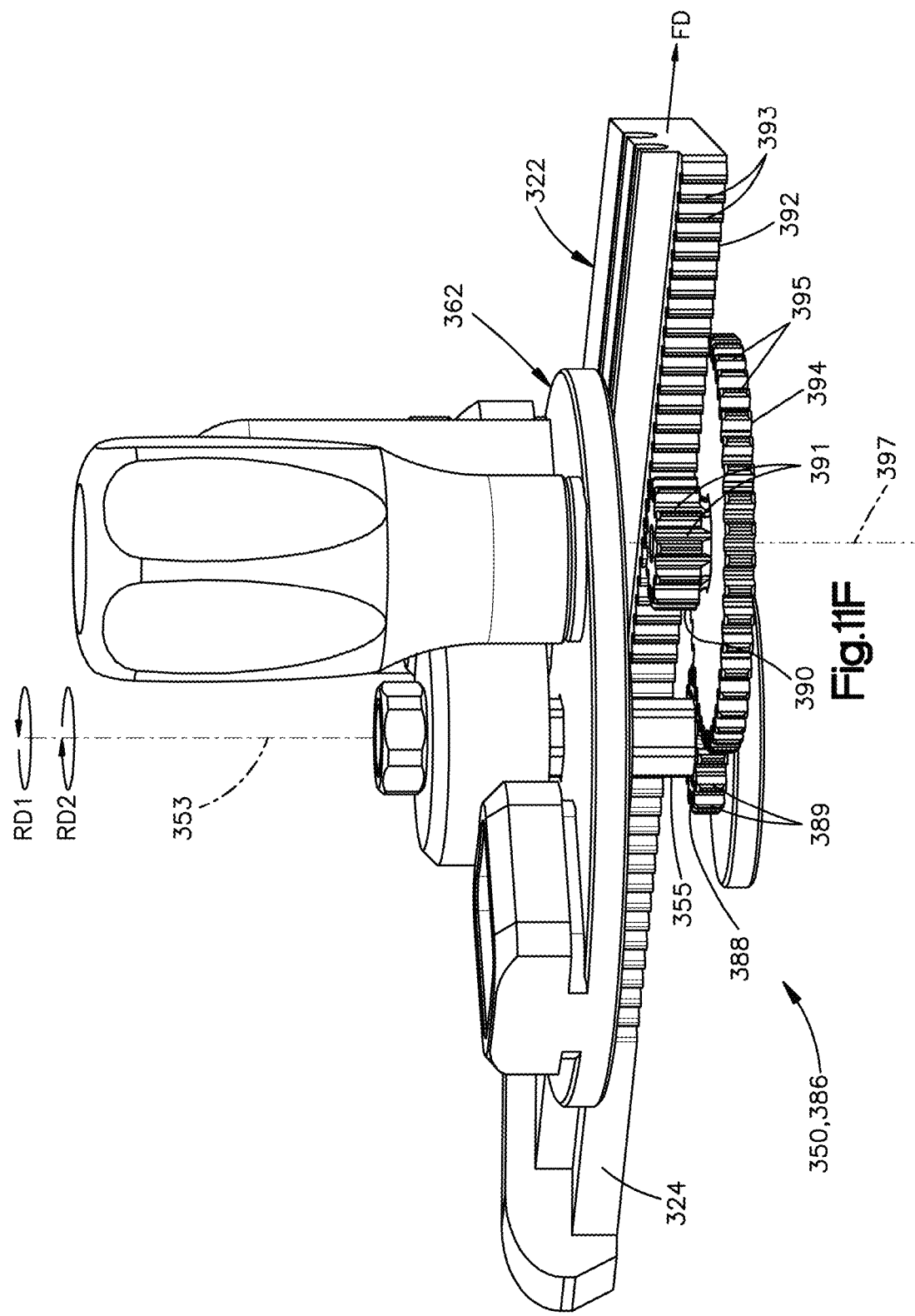

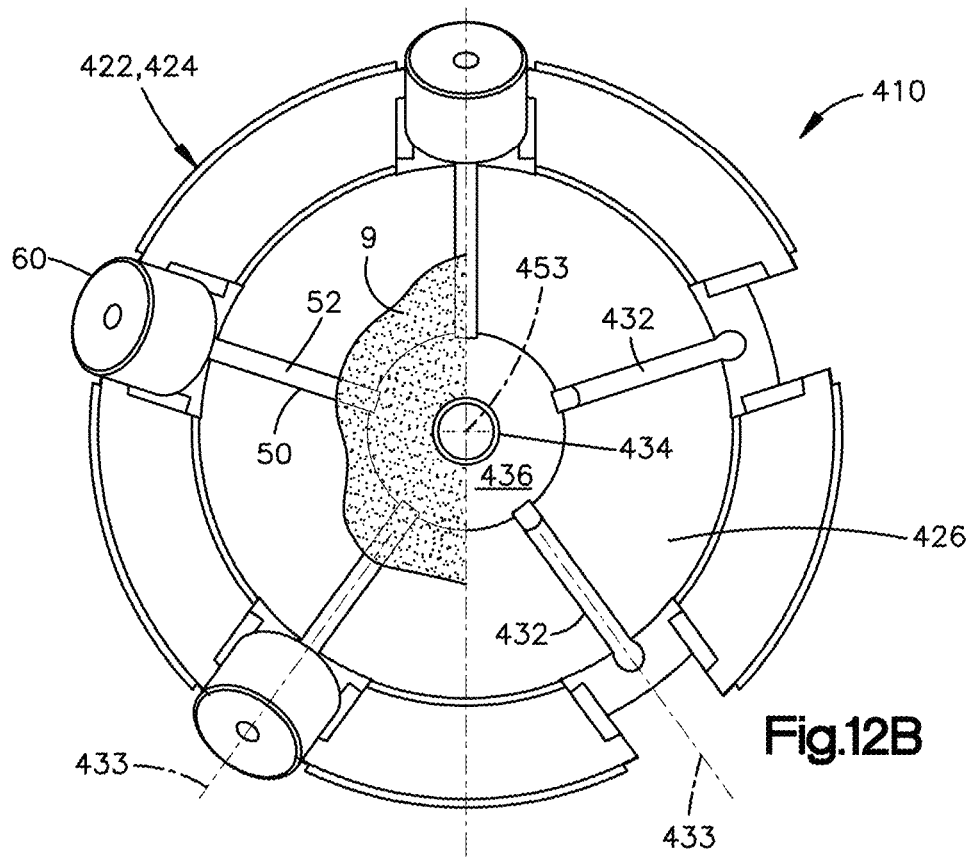
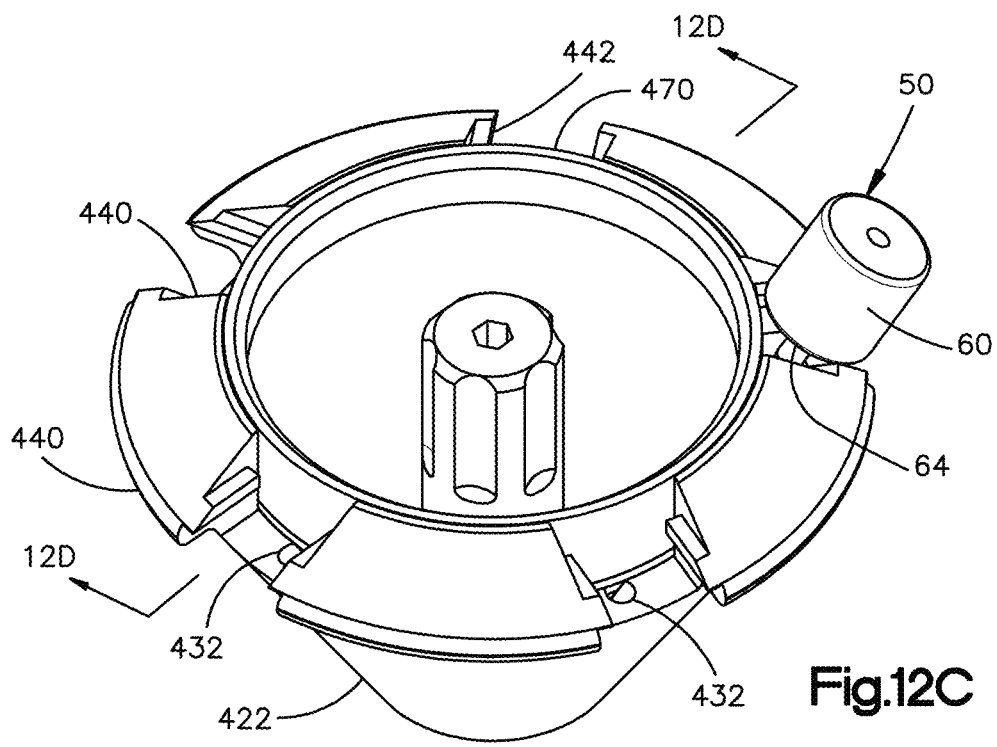

BIOMATERIAL DELIVERY DEVICE, AND RELATED SYSTEMS AND METHODS

TECHNICAL FIELD

The present invention relates to devices for delivering flowable biomaterial, such as bone graft, into target locations within the body of a patient, as well as to assemblies for loading flowable biomaterial into the delivery devices.

BACKGROUND

Removal of an intervertebral disc is often desired if the disc degenerates. Spinal fusion may be used to treat such a condition and involves replacing a degenerative disc with a device such as a fusion cage or other spacer that restores the height of the disc space and allows bone growth around and/or through the device to fuse the adjacent vertebrae. Spinal fusion procedures attempt to restore normal spinal alignment, stabilize the spinal segment for proper fusion, create an optimal fusion environment, and allows for early active mobilization by minimizing damage to spinal vasculature, dura, and neural elements. When spinal fusion meets these objectives, healing quickens and patient function, comfort and mobility improve.

Bone growth inducing material, such as bone graft and/or bone graft substitutes, is commonly used in connection with fusion cages to encourage bone growth around and/or through the fusion cage or spacer to enhance the speed and strength at which the adjacent vertebrae fuse together. In particular, the disc space evacuated by resected disc material (e.g., nucleus pulposus and/or anulus fibrosis) can be filled with bone growth inducing material before or after insertion of the cage or spacer into to the disc space. Additionally or alternatively, the cage or spacer can be packed with bone growth inducing material prior to insertion.

Modern surgical approaches for spinal treatment, including spinal fusion, have included efforts to reduce the size of the incision and thereby also reduce, among other things, disruption to tissue. Such techniques are commonly referred to as "minimally invasive" (MIS) approaches, and require instrumentation small enough to be introduced through a small incision and long enough to access the surgical site, such as the disc space, from the skin surface. Reducing the size of instrumentation for delivering bone growth inducing material into the disc space presents challenges, particularly because such materials are often highly viscous and fibrous and can thus tend to block or clog the delivery instrument.

SUMMARY

According to an embodiment of the present disclosure, a system for delivering flowable biomaterial into an intervertebral disc space between an upper vertebral body and a lower vertebral body of a patient includes a plurality of delivery bodies each configured for delivering the biomaterial and each defining: a proximal end, a distal end spaced from the proximal end along a longitudinal direction, a cannulation extending from the proximal end to at least one opening adjacent the distal end, and a distal region including a tip that extends to the distal end. The distal region defines a maximum height at a location proximally spaced from the distal end. The maximum height is measured along a second direction perpendicular to the longitudinal direction. The maximum heights of at least some of the distal regions of the plurality of delivery bodies are different from one another, and the distal regions are configured to provide feedback indicating a distance between the upper and lower vertebral bodies along a cranial-caudal direction. The system includes a carrier that defines a channel elongate along the longitudinal direction. The carrier is configured for insertion within the cannulation of any of the plurality of delivery bodies to carry the material within the cannulation. The system also includes an advancement member configured for insertion within the cannulation of any of the plurality of delivery bodies so as to forcibly advance the material from the cannulation, through the at least one opening, and into the interverbal disc space.

According to another embodiment of the present disclosure, a system for loading flowable biomaterial into an instrument for subsequent delivery into an intervertebral disc space includes a loading tray having a tray body that has a floor surface configured to receive the biomaterial. The tray body also includes a plurality of sidewalls at a periphery of the floor surface. The plurality of sidewalls and the floor surface cooperatively define a tray volume. At least one of the plurality of sidewalls defines at least one access opening extending therethrough. The tray body also includes at least one slot that is elongate along a longitudinal direction, recessed from the floor surface, open to the tray volume, and in communication with the at least one access opening. The system also includes an instrument having a portion that is elongate and is configured for insertion within the at least one elongate slot along the longitudinal direction. The instrument defines a channel, where the channel is configured such that, when the instrument resides in the at least one slot, the channel is elongate along the longitudinal direction and is orientable so as to be open to the tray volume.

According to an additional embodiment of the present disclosure, an assembly for loading flowable biomaterial into an instrument for subsequent delivery to a target location within a patient includes a loading device that has a housing which has a base surface. The loading device includes a body portion that defines at least one elongate slot that is configured to receive an elongate portion of an instrument having an open, elongate channel. The loading device also includes a rotary member coupled to the housing such that a volume of space is at least partially defined between the rotary member and the base surface, where the volume of space is configured to contain the biomaterial. The rotary member includes at least one member configured to move a quantity of the biomaterial from the volume of space into the at least one elongate slot responsive to relative rotation between the rotary member and the housing.

According to a further embodiment of the present disclosure, an assembly for loading flowable biomaterial into an instrument for subsequent delivery to a target location within a includes a loading device that has a housing which has an inner surface within an interior of the housing. A plurality of elongate slots are defined within the inner surface and are each configured to receive an elongate portion of an instrument having an open, elongate channel. The loading device includes a rotary member coupled to the housing such that a volume of space is defined between the rotary member and the housing, wherein the volume of space is configured to contain the biomaterial and is in communication with the at least one slot. The rotary member includes at least one member configured to move a quantity of the biomaterial from the volume of space into the plurality of elongate slots responsive to relative rotation between the rotary member and the housing.

BRIEF DESCRIPTION OF THE DRAWINGS

The foregoing summary, as well as the following detailed description of illustrative embodiments of the present application, will be better understood when read in conjunction with the appended drawings. For the purposes of illustrating the structures of the present application, there is shown in the drawings illustrative embodiments. It should be understood, however, that the application is not limited to the precise arrangements and instrumentalities shown. In the drawings:

FIG. 6A is a perspective view of an instrument assembly for delivering flowable biomaterial to an intervertebral disc space of a patient, wherein the instrument includes a switch mechanism for retaining the biomaterial within the instrument assembly while the carrier is withdrawn from the instrument assembly, in which the mechanism is shown in an open position, according to yet another embodiment of the present disclosure;

FIG. 6B is a sectional perspective view of the switch mechanism illustrated in FIG. 6A, shown in a closed position;

FIG. 8A is an exploded perspective view of an instrument assembly employing a rotary mechanism for delivering flowable biomaterial to the intervertebral disc space, according to an additional embodiment of the present disclosure;

FIG. 11A is a perspective view of another example of a loading device for loading flowable biomaterial into the carrier of the instrument assembly illustrated in FIG. 1A, according to another embodiment of the present disclosure;

FIG. 11F is a perspective view of a rotary mechanism of the loading device illustrated in FIG. 11A;

FIG. 12B a top plan view of a housing of the loading device illustrated in FIG. 12A;

FIG. 12C is a perspective view of the loading device illustrated in FIG. 12A.

DETAILED DESCRIPTION OF ILLUSTRATIVE EMBODIMENTS

Figure 1A:
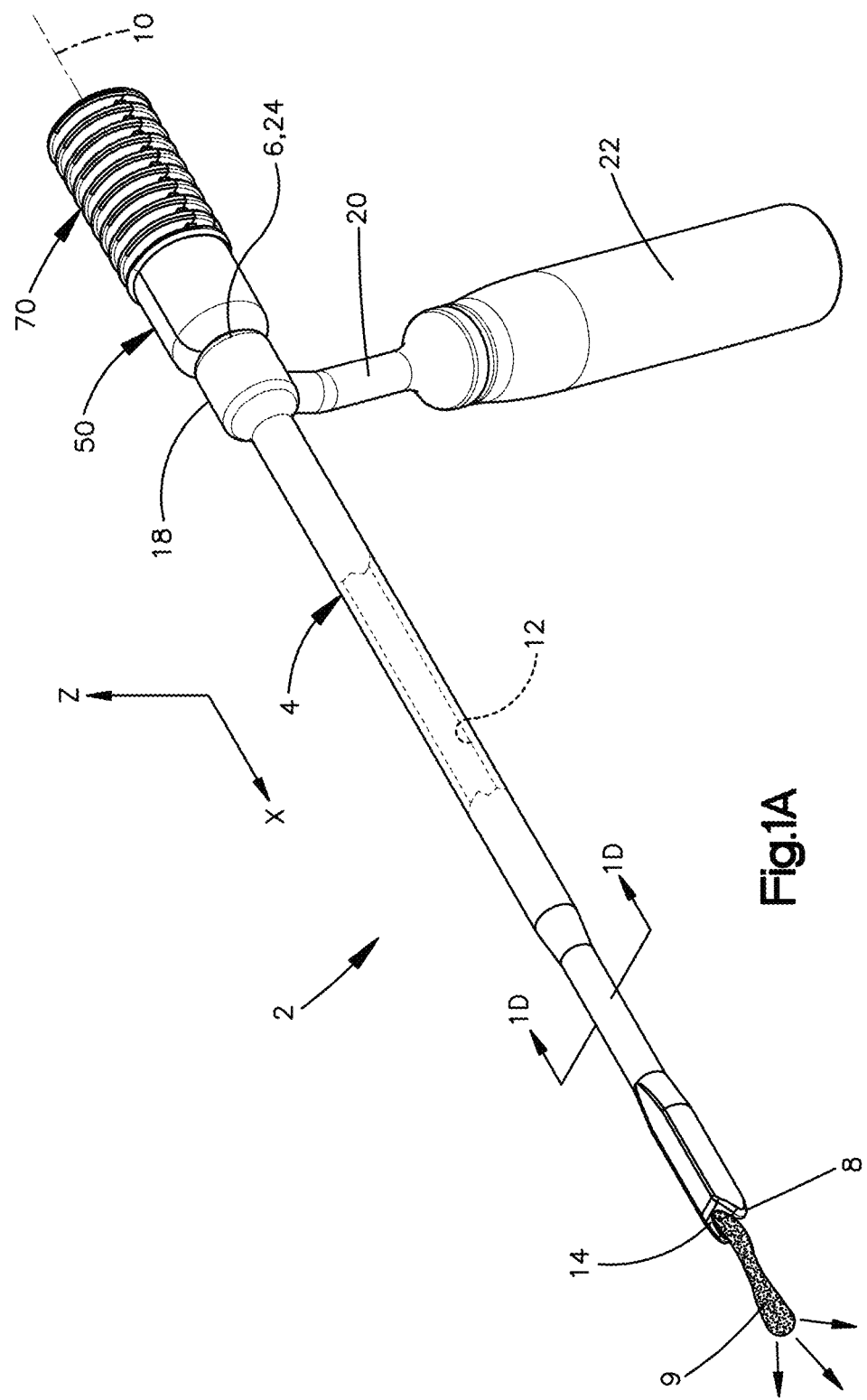
FIG. 1A is a perspective view of an instrument assembly for delivering flowable biomaterial to an intervertebral disc space of a patient, according to an embodiment of the present disclosure.

The present disclosure can be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the scope of the present disclosure. Also, as used in the specification including the appended claims, the singular forms "a," "an," and "the" include the plural, and reference to a particular numerical value includes at least that particular value, unless the context clearly dictates otherwise.

The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

The terms "approximately" and "substantially", as used herein with respect to dimensions, angles, and other geometries, takes into account manufacturing tolerances. Further, the terms "approximately" and "substantially" can include 10% greater than or less than the stated dimension or angle. Further, the terms "approximately" and "substantially" can equally apply to the specific value stated.

The embodiments described below with reference to FIGS. 1A through 8C pertain to instrumentation, such as instruments, instrument systems, and/or instrument assemblies, for delivering flowable biomaterial into the anatomy of a patient, particularly, but not limited to, an intervertebral disc space. As used herein, the term "biomaterial" refers to a natural or synthetic material that is suitable for introduction into living tissue, particularly as part of a medical implant, and includes any material for infilling a bone, an in-situ hardenable material, a bone growth inducing material, such as bone graft, including autograft and allograft bone, and can include "fillers" such as filaments, fibers, microspheres, powders, granular elements, flakes, chips, tubules and the like, as well as other chemicals, pharmacological agents and/or other bioactive agents. As used herein, the term "flowable biomaterial" refers to a biomaterial having a material continuum that is unable to withstand a static shear stress and responds with an irrecoverable (i.e., fluidic) flow—unlike an elastic material or elastomer that responds to shear stress with a recoverable deformation—and includes gels, suspensions, powders, and the like.

These embodiments pertain to biomaterial delivery instruments with various distal opening geometries for expelling the biomaterial favorably into the intervertebral disc space or other anatomy.

These embodiments also pertain to delivery instruments with distal geometries that allow the delivery instruments to double as trial instruments, such as for ascertaining the disc height between adjacent vertebral bodies, for example. Such trial-capable distal geometries can be particularly beneficial in that they can effectively eliminate a subsequent trialing procedure for an implant, such as an intervertebral fusion cage, such as an expandable fusion cage, to be inserted within the intervertebral disc space.

These embodiments also pertain to delivery instruments having retention mechanisms that iterates between an open position, in which a loading instrument carrying a quantity of biomaterial is insertable within the instrument, and a closed position, in which the biomaterial is retained within the delivery instrument while the loading instrument is retracted therefrom.

These embodiments also pertain to features for reducing surface friction between the biomaterial and the delivery instruments.

The embodiments described below with reference to FIGS. 9A through 12D pertain to biomaterial-loading systems, including biomaterial-loading devices and assemblies, for depositing biomaterial in one or more loading instruments for subsequent insertion within one or more delivery instruments.

Referring now to FIG. 1A, an exemplary embodiment of an instrument assembly 2 is shown for dispensing of otherwise delivering flowable biomaterial 9 to an intervertebral disc space (hereinafter referred to as the "disc space") between a superior vertebral body and an inferior vertebral body. The flowable biomaterial 9 is also referred to herein simply as "the material" 9, and can include any of the flowable biomaterials described above. It should also be appreciated that the instrument assembly 2 can be referred to as a "system", and includes instrumentation, such as an outer delivery body 4, a carrier 50 that is insertable within the delivery body 4 for loading biomaterial 9 in the delivery body 4, and an advancement member 70 insertable within the carrier 50 and delivery body 4 for advancing the biomaterial 9 through the delivery body 4 to the disc space. Each of the delivery body 4, the carrier 50, and the advancement member 70 can be referred to herein as an "instrument".

The outer delivery body 4 has a proximal end 6 and a distal end 8 spaced from the proximal end 6 along a longitudinal direction X that is oriented along a central axis 10 of the delivery body 4. It should be appreciated that the central axis 10 of the delivery body 4 can effectively define the central axis of the instrument assembly 2. The delivery body 4 defines an outer surface 11 and a cannulation 12 opposite the outer surface 11 with respect to a radial direction R perpendicular to the central axis 10 (and thus also perpendicular to the longitudinal direction X). Accordingly, the delivery body 4 can also be referred to as a "cannulated" body. The cannulation 12 extends from the proximal end 6 to at least one opening 14 at a first location 16a at or adjacent the distal end 8 of the delivery body 4. The cannulation 12 is in fluid communication (also referred to herein simply as "communication") with the opening 14 so that the biomaterial 9 can be directed through the cannulation 12 and out the opening 14 and into the disc space. As shown, the at least one opening 14 can be a single opening that is open along the central axis 10 (i.e., the central axis 10 extends through the opening 14), or that is at least open along the longitudinal direction X. Thus, the opening 14 can be referred to as an "axial opening". In other embodiments, the at least one opening 14 can have other configurations, as described in more detail below.

The delivery body 4 can define a mounting formation 18 at the proximal end 6. The mounting formation 18 can be configured to receive a handle component, such as a handle connection 20 attached to a handle 22, as shown. The mounting formation 18 can also define a proximal surface 24 that defines the proximal end 6 of the delivery body 4.

Figure 1B:
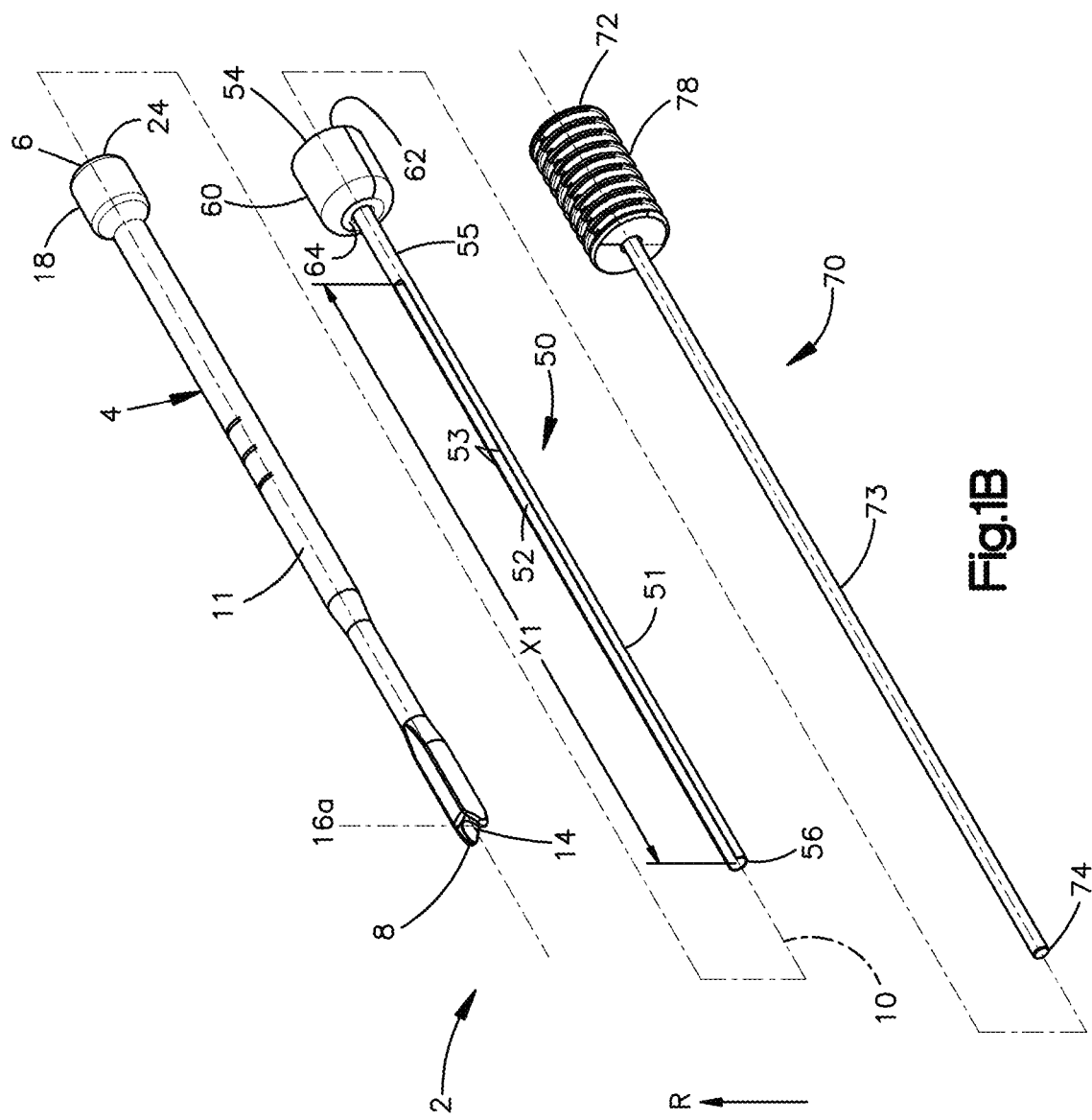
FIG. 1B is an exploded perspective view of a delivery body, a carrier, and an advancement member of the instrument assembly illustrated in FIG. 1A.
Figure 1C:
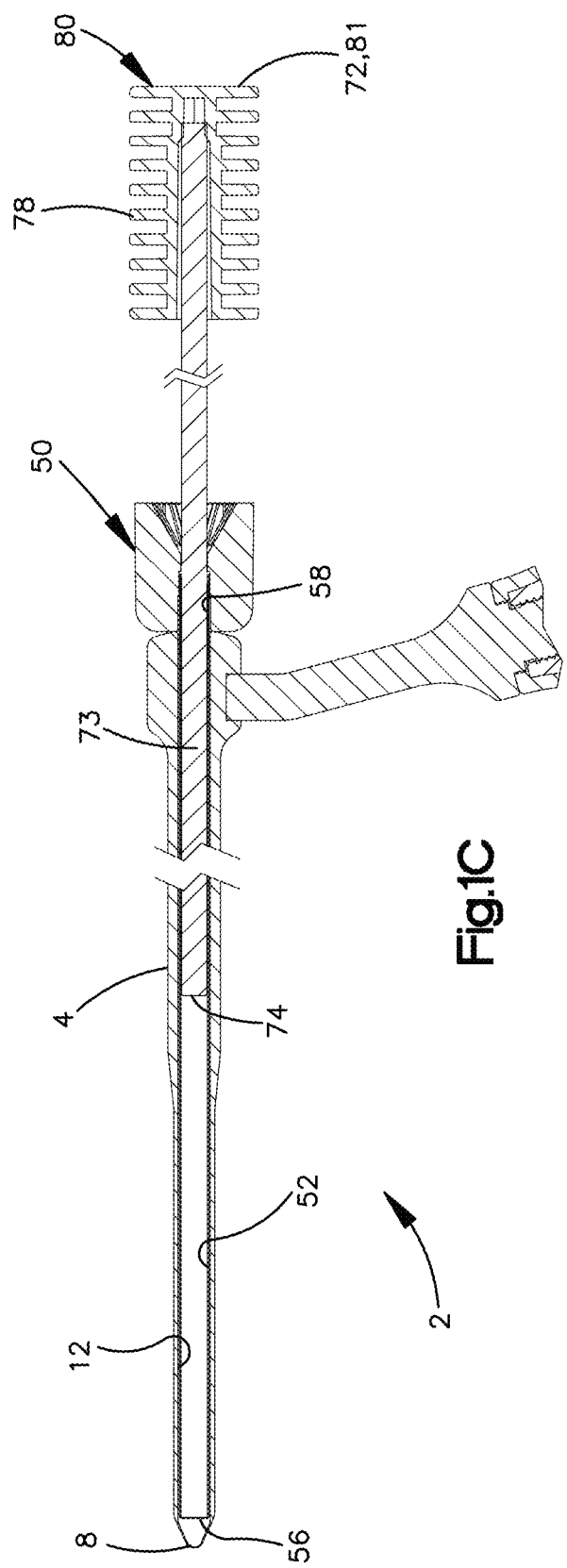
FIG. 1C is a sectional side view of the instrument assembly illustrated in FIG. 1A, showing the advancement member less than fully inserted within the delivery body.
Figure 1D:
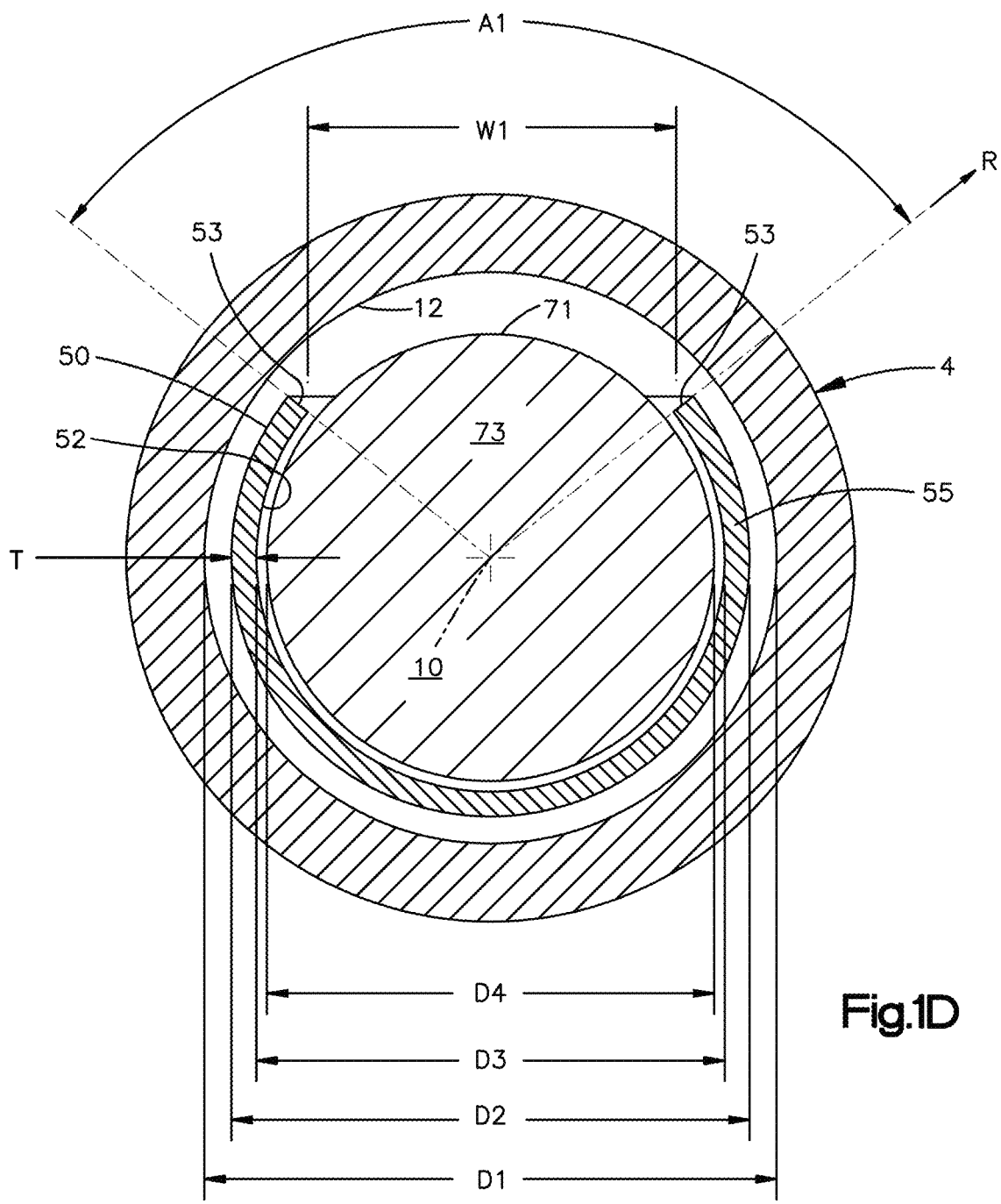
FIG. 1D is a sectional end view of a the instrument assembly taken along section line 1D-1D illustrated in FIG. 1B.

Referring now to FIGS. 1B and 1C, the system includes a carrier 50 that includes an elongate body portion 55 that is sized for insertion within the cannulation 12 of the delivery body 4 along the central axis 10. The elongate body portion 55 defines an outer surface 51 and a channel 52 that is elongate along the longitudinal direction X. The channel 52 is configured to carry or "load" the biomaterial 9 into the cannulation 12 from the proximal end 6 of the delivery body 4. The elongate body portion 55 also defines an elongate channel opening 53 that is elongate along the longitudinal direction X and is in communication with the channel 52 along a direction offset from the longitudinal direction X, such as the radial direction R, for example. In the illustrated embodiment, the elongate channel opening 53 is defined by surfaces of the elongate body portion 55 that extend inwardly from the outer surface 51 of the elongate body portion 55 to the channel 52, such as along the radial direction R, as shown in FIG. 1D. The elongate channel opening 53 allows the channel 52 to be open to an exterior of the elongate body portion 55 along the direction offset from the longitudinal direction X. In this manner, the channel 52 is also open to the cannulation 12 along such a direction when the elongate body portion 55 is inserted within the delivery body 4. The elongate channel opening 53 (and thus the channel 52) defines a length X1 measured along the longitudinal direction X. The carrier 50 defines a proximal end 54 and a distal end 56 spaced from each other along the longitudinal direction X. The carrier 50 can define a central bore 58 that extends from the proximal end 54 at least to, and in open communication with, the channel 52. As shown, the central bore 58 and the channel 52 can extend to the distal end 56 of the carrier 50.

The carrier 50 can include a stop member 60 that defines the proximal end 54 of the carrier 50. The stop member 60 can define a proximal surface 62 and a distal surface 64 spaced from each other along the longitudinal direction X. The proximal surface 62 can define the proximal end 54 of the carrier 50. In the illustrated embodiments, the carrier 50 is configured to advance within the cannulation 12 of the delivery body 4 until the distal surface 64 of the stop member 60 abuts the proximal surface 24 of the mounting formation 18 of the delivery body 4, which defines a fully inserted position of the carrier 50 relative to the delivery body 4.

The system also includes an advancement member 70 that is configured to be inserted within the cannulation 12 of the delivery body 4 along the central axis 10 and advance the biomaterial 9 loaded in the cannulation 12 distally to and through the opening 14 and into the disc space. It should be appreciated that the central axis 10 is preferably substantially coincident with respective central axes of the carrier 50 and the advancement member 70 when they are fully inserted within the delivery body 4. Accordingly, the central axis 10 can also be referred to as the central axis of the carrier 50 and/or the central axis of the advancement member 70. The advancement member 70 defines a proximal end 72 and a distal end 74 spaced from each other along the longitudinal direction X. In the presently illustrated embodiment, the advancement member 70 is configured to advance within the central bore 58 and the channel 52 of the carrier 50, while the carrier 50 is inserted within the cannulation 12 of the delivery body 4, and to push the biomaterial 9 through and out the cannulation 12 through the opening 14. Thus, the advancement member 70 can include a push rod 73, the distal end 74 thereof defining a distal surface 76 configured to push or otherwise drive the biomaterial 9 distally through the carrier channel 52 and thus also through the cannulation 12. The advancement member 70 can include a force transmission member 78 at the proximal end 72. It is to be appreciated that the force transmission member 78 can be coupled to the push rod 73, or the force transmission member 78 and the push rod 73 can alternatively be monolithic. The force transmission member 78 can include an impaction pad 80 that presents a proximal surface 81 for receiving impaction forces to drive the push rod 73, and thus the biomaterial 9, distally through the cannulation 12, as needed.

With reference to FIG. 1D, the channel 52 of the carrier 50 has a generally trough-like shape in a reference plane orthogonal to the central axis 10. The elongate channel opening 53 defines an opening angle A1 that can be in a range of about 30 degrees to about 180 degrees about the central axis 10. In some embodiments, the opening angle A1 is in a range of about 90 degrees to about 115 degrees. In further embodiments, the opening angle A1 is in a range of about 100 degrees to about 105 degrees. The elongate body portion 55 of the carrier 50 also defines a thickness T1 measured along the radial direction R. The thickness T1 is preferably selected to provide the elongate body portion 55 with outward flexibility along the radial direction R, as described in more detail below.

The cannulation 12 of the delivery body defines an inner diameter D1, the outer surface 51 of the carrier 50 defines an outer diameter D2, the channel 52 and the central bore 58 of the carrier 50 defines an inner diameter D3, and the outer surface 71 of the push rod 73 defines an outer diameter D4. The inner diameter D1 of the cannulation 12 and the outer diameter D2 of the carrier 50 are cooperatively sized to allow the carrier 50 to be inserted smoothly within the cannulation 12 of the delivery body 4. The inner diameter D3 of the channel 52 and the outer diameter D4 of the push rod 73 are cooperatively sized to allow the push rod 73 to advance smoothly along the longitudinal direction X within the channel 52 to push the biomaterial 9 distally through the channel 52 and cannulation 12 and out the at least one opening 14 and into the disc space. The elongate channel opening 53 defines a width W1 measured along a lateral direction Y perpendicular to the longitudinal direction Y.

The elongate body portion 55 of the carrier 50 can be sufficiently long to extend from an exterior of the patient to the disc space. The dimensions of the carrier 50, particularly the length X1 and inner diameter D3 of the channel 52, can be tailored as necessary for carrying a desired quantity of biomaterial 9, such as a quantity in a range of about 0.75 $cm^3$ to about 15 $cm^3$, particularly in a range of about 1.0 $cm^3$ to about 12.0 $cm^3$, and more particularly in a range of about 2.5 $cm^3$ to about 8.0 $cm^3$. The channel length X1 can be in a range of about 50 mm to about 400 mm, particularly in a range of about 150 mm to about 350 mm, and more particularly in a range of about 200 mm to about 310 mm. The inner diameter D3 of the channel 52 can be in a range of about 3.0 mm to about 6.0 mm, particularly in a range of about 4.0 mm to about 5.0 mm, and more particularly about 4.5 mm. It is to be appreciated that the foregoing dimensional ranges are provided as examples, and one or more and up to all of the foregoing dimensions can be scaled upward or downward in size as needed, including outside the foregoing ranges.

It is to be appreciated that the cannulation 12 of the present embodiment preferably has a substantially constant inner diameter D1 for facilitating smooth axial advancement of the carrier 50 therein, as well as for smooth axial advancement of the biomaterial 9 along the channel 52 disposed within the cannulation 12. Similarly, the channel 52 and central bore 58 of the carrier 50 preferably have a substantially constant inner diameter D3 to facilitate smooth axial advancement of the biomaterial 9 and push rod 73 therethrough. Additionally, the surfaces of the cannulation 12 and channel 52 and central bore 58 can be finished according to a finishing process for reducing the surface finish roughness of each such surface so as to reduce friction with the biomaterial 9.

It is also to be appreciated that the cannulation 12 can alternatively have a non-circular shape in a reference plane orthogonal to the central axis 10, such as a square or rectangular shape or other polygonal shape, by way of non-limiting examples. In such embodiments, one or more and up to all of the elongate carrier body 55, the carrier channel 52, and the push rod 73 can have corresponding cross-sectional shapes.

Figure 1E:
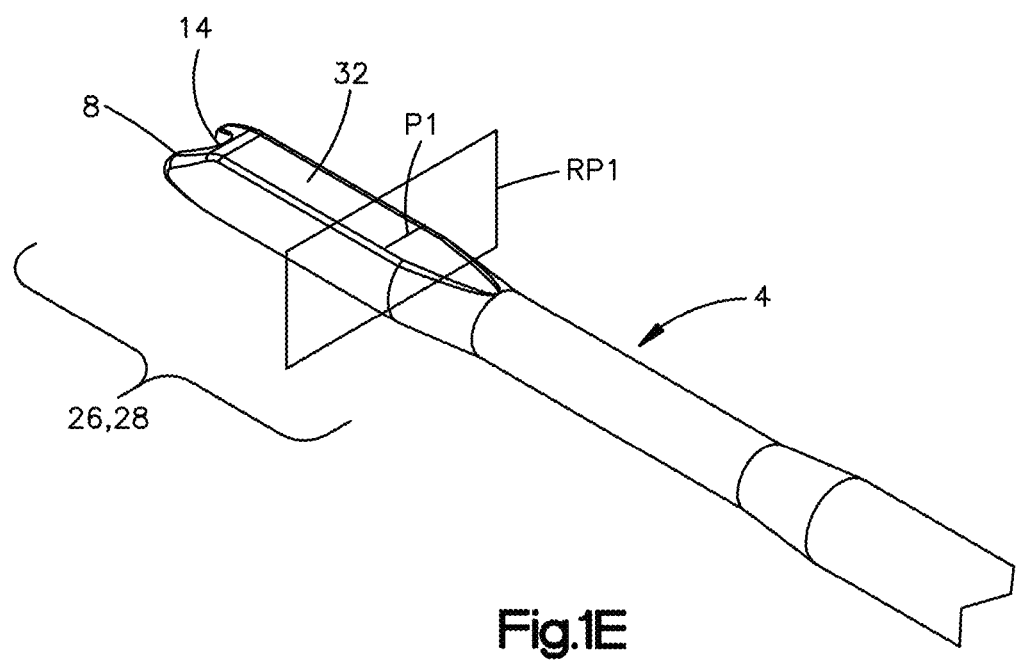
FIG. 1E is an enlarged perspective view of a distal region of the instrument assembly illustrated in FIG. 1A.
Figure 1F:
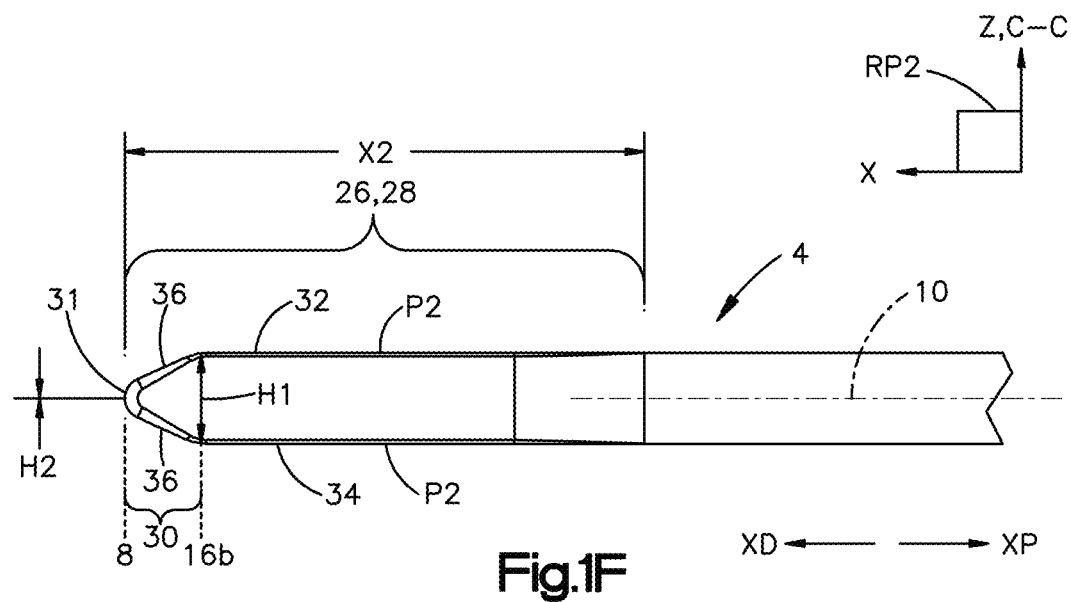
FIG. 1F is a side plan view of the distal region of the instrument assembly illustrated in FIG. 1C.

Referring now to FIGS. 1E and 1F, a distal region 26 of the delivery body 4 is configured to advance within the disc space during an intervertebral biomaterial delivery procedure, such as an intervertebral bone grafting procedure. The distal region 26 includes a tip 30 that defines the distal end 8 of the delivery body 4. The tip 30 can also be referred to as a "distal tip", "leading tip", and/or "insertion tip". The tip 30 defines a maximum or first height H1. The tip 30 can also taper distally to a second height H2 that is less than the first height H1. In such embodiments, the first height can be located at a second location 16b proximally spaced from the distal end 8, and the second height H2 can be located at the distal end 8. In some such embodiments, the tip 30 can taper distally to a point or a rounded distal end 8 that can have a nominal second height H2, or a second height H2 that is zero or substantially zero. For example, in the presently shown embodiment, the tip 30 can taper distally to a rounded or otherwise pointed nose 31 at the distal end 8. The first and second heights H1, H2 are each measured along a vertical direction Z that is perpendicular to the central axis 10 (and thus also perpendicular to the longitudinal direction X) and perpendicular to the lateral direction Y. It should be appreciated that the second direction Z is configured to coincide with the cranial-caudal direction C-C when the delivery body 4 is advanced within the patient. Accordingly, the second direction Z can also be referred to as a vertical direction Z.

As used herein, the terms "proximal", "proximally", "proximally spaced", and their derivatives refer to spacing along a proximal direction XP oriented along the longitudinal direction X from the distal end 8 to the proximal end 6. Additionally, as used herein, the terms "distal", "distally", "distally spaced", and their derivatives refer to spacing along a distal direction XD oriented along the longitudinal direction X from the proximal end 6 to the distal end 8. It should be appreciated that the proximal end distal directions XP, XD are each monodirectional components of the longitudinal direction X, which is bi-directional.

The distal region 26 defines a first or superior contact surface 32 and a second or inferior contact surface 34 opposite each other along the second direction Z. Preferably, the first and second contact surfaces 32, 34 are spaced from each other along the second direction Z by the first height H1. The first and second contact surfaces 32, 34 are configured to face, and optionally contact, the opposed endplates of the superior and inferior vertebral bodies, respectively. The distal region 26 can define a distance X2, measured along the longitudinal direction X from the distal end 8 of the delivery body 4 to a proximal end 35 of the first and second contact surfaces 32, 34. The first and second contact surfaces 32, 34 can each have a profile P1 that is substantially linear in a reference plane RP1 orthogonal to the central axis 10, as shown in FIG. 1E, although other profiles in the orthogonal reference plane RP1 are also within the scope of the present disclosure. For example, the first and second contact surfaces 32, 34 can have a crowned (i.e., an arcuate, convex) profile in the orthogonal reference plane. The first and second contact surfaces 32, 34 can also each have a profile P2 that is substantially linear in a reference plane RP2 that extends along the central axis 10 (and thus along the longitudinal direction X) and the second direction Z. The tip 30 also preferably defines tapered surfaces 36 extending from the second location 16b to the distal end 8. Preferably, the tip 30 employs the tapered surfaces 36 in combination with a pointed nose 31, whereby the tip 30 is configured to enter the disk space and distract the adjacent vertebral bodies away from one another along the cranial-caudal direction to the extent desired, such as for preparing the disc space to receive a fusion cage, such as an expandable fusion cage, for example. The tip 30 can also be configured to allow for additional distraction as the distal region 26 is rotated about the central axis 10. The tapered surfaces 36 can also advantageously guide the tip 30, and thus also the distal region 26, into the disc space, if need be, as the tapered surfaces 36 engage the adjacent superior and inferior vertebral bodies.

Figure 2A:
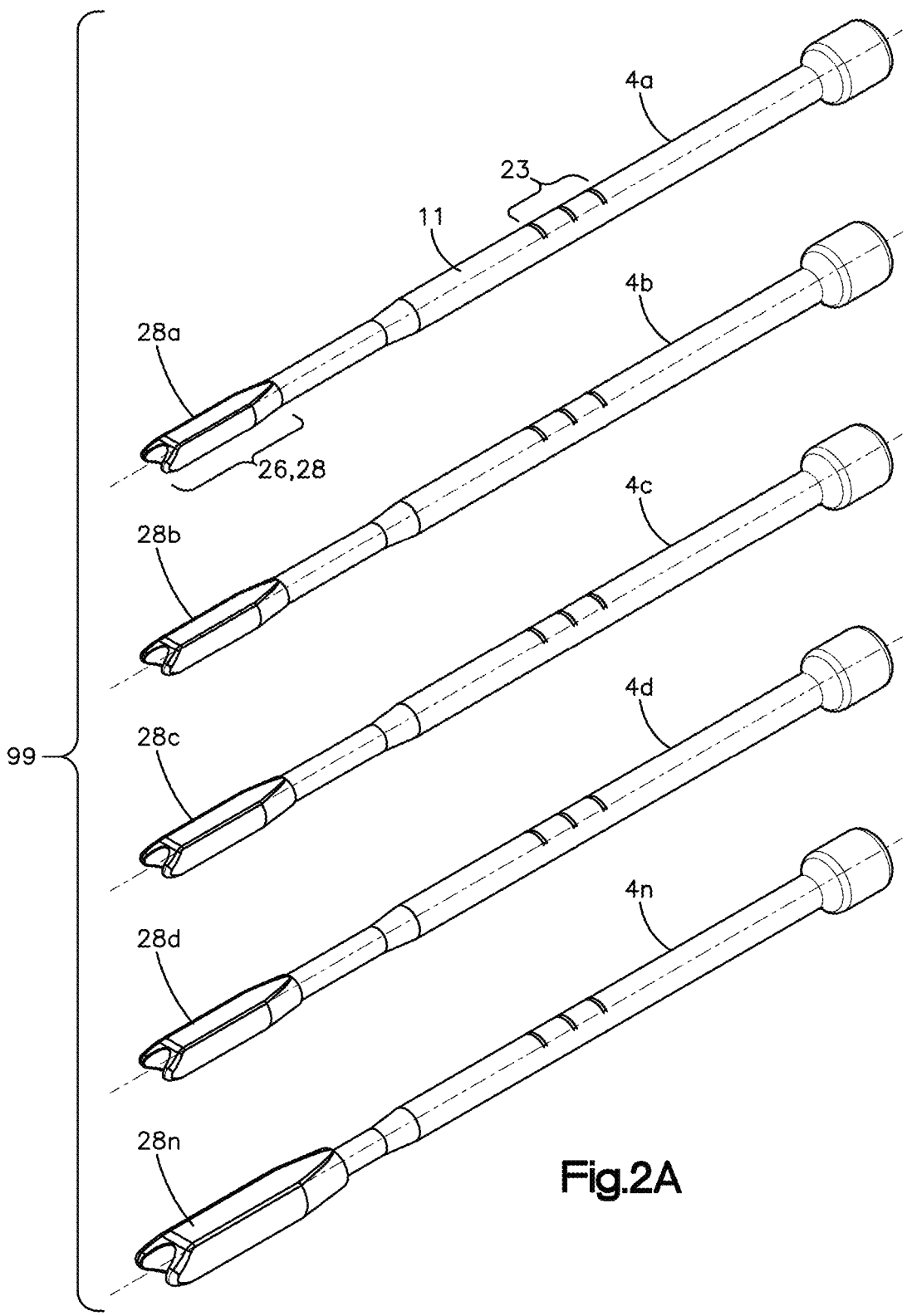
FIG. 2A is a perspective view of a kit that includes a plurality of delivery bodies having different dimensions, according to an embodiment of the present disclosure.
Figure 2B:
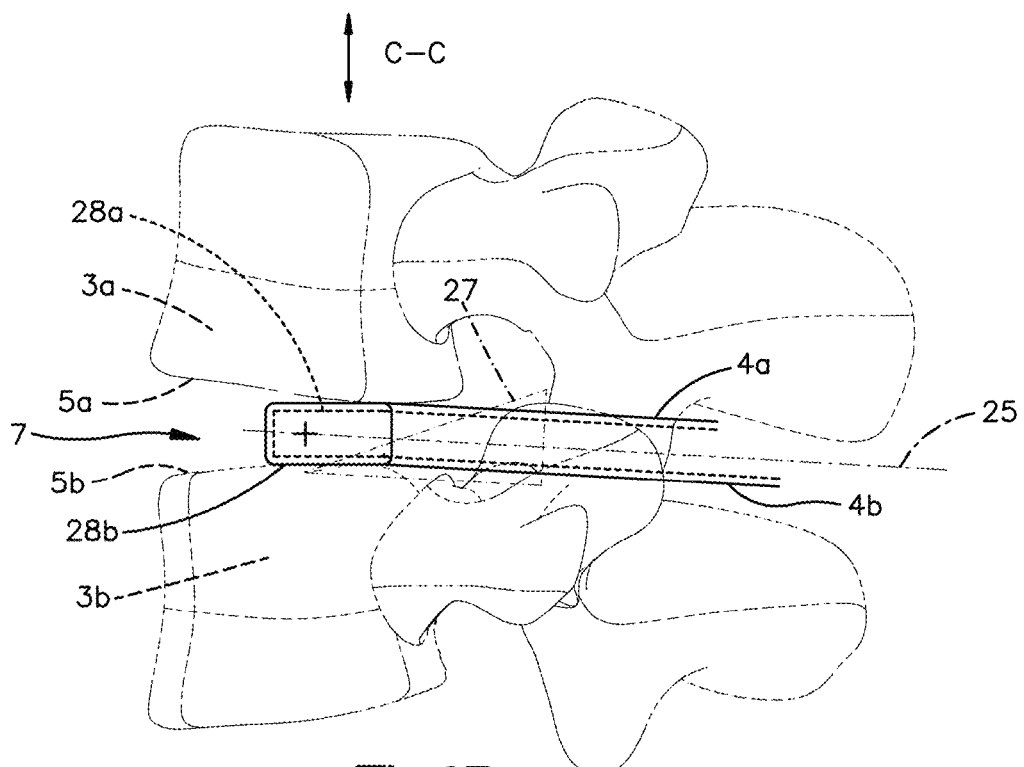
FIG. 2B is a perspective view of distal regions of a pair of successive, respective delivery bodies of the kit illustrated in FIG. 2A, in which the distal regions are employed as trial implant portions positioned in an intervertebral disc space between adjacent vertebral bodies, along an insertion axis that extends through the extended kambin's triangle, according to an embodiment of the present disclosure.
Figure 2C:
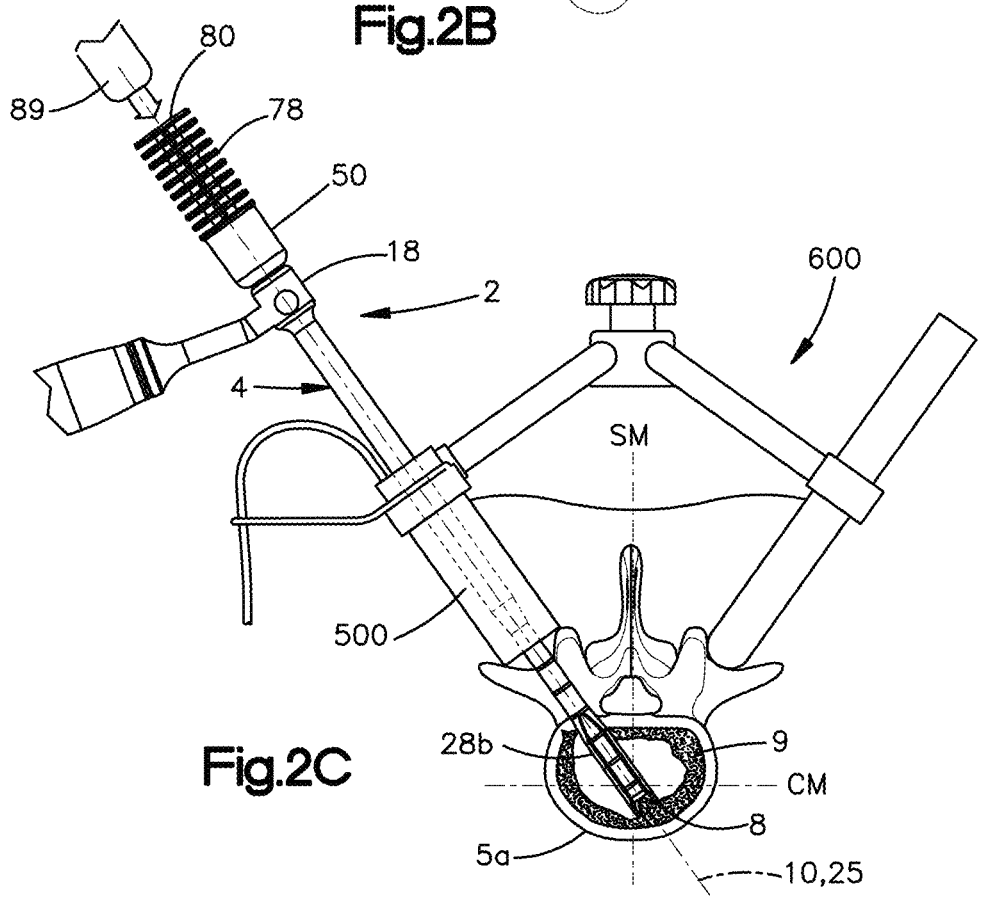
FIG. 2C is a schematic plan view of the instrument assembly illustrated in FIG. 1A delivering flowable biomaterial into an intervertebral disc space along the insertion axis shown in FIG. 2B.

Referring now to FIGS. 2A through 2C, one significant advantage provided by the design of the delivery bodies 4 disclosed herein is that the distal region 26 can be utilized as a trial member or portion 28 of the delivery body 4, as will now be described.

As shown in FIG. 2A, the delivery body 4 can be provided in a kit system 99 that includes a plurality of delivery bodies 4a-n, each optionally being configured generally similarly to one another, and each for delivering biomaterial 9 to an intervertebral disc space 7 between a superior vertebral body 3a and an adjacent inferior vertebral body 3b. The delivery bodies 4a-n of the kit system 99 have respective trial portions 28a-n, which preferably each define at least one dimension, such as the maximum height H1, that is different than that of at least one other of the trial portions 28a-n. The at least one dimension can also include the length X2 of the trial portions 28a-n. Accordingly, the trial portions 28a-n can be configured to provide feedback to a physician at least regarding the spacing or "disc height" between the respective endplates 5a, b of the superior and inferior vertebral bodies 3a, b that define a disc space along the cranial-caudal direction C-C of the patient.

The feedback provided by the trial portions 28a-n preferably includes visual feedback of the disc height. In such embodiments, the trial portions 28a-n can be formed from a material that is visible under radiographic imaging, such as titanium, stainless steel, or the like. The at least one opening 14 of the trial portions 28a-n, when viewed in conjunction with lateral and frontal X-rays, assists in the optimum positioning of the respective trial portion 28a-n relative to the superior and inferior vertebral bodies. The trial portions 28a-n can also include one or more markers or other features that are visible under radiographic imaging, such as fluoroscopy, for assisting in the optimal positioning of the trial portions 28a-n of the delivery bodies 4a-n. The radiographic visibility of each trial portions 28a-n allows a physician to use one or more such trial portions 28a-n in succession to gauge the disc height. Thus, an additional advantage of these trial portion 28a-n is that the height of a subsequent intervertebral fusion cage can be determined during the biomaterial 9 delivery phase of a multi-phase intervertebral procedure, which can eliminate the need for a separate fusion cage height trialing step.

The delivery body 4 can also include additional visual indicia, such as a series of hatch marks 23 having uniform spacing, such as at 5 mm or 10 mm increments, for example, provided on the outer surface 11 of the delivery body 4. The hatch marks 23 can be employed for indicating the depth at which the trial portion 28a-n engages the vertebra, as well as the depth at which the distal end 8 advances within the disc space. The hatch marks 23 can also be used in combination with radiographic imaging to ascertain the insertion depth to a target location of the disk space.

Referring now to FIGS. 2B and 2C, an example method of using the instrument assembly 2 in a minimally invasive (MIS) procedure will now be described. A spinal disc in need of repair or replacement is identified and an at least partial discectomy is performed through a small incision and along a spinal approach axis 25, preferably via a transforaminal approach, such as through the kambin's triangle 27. It should be appreciated, however, that other approaches are within the scope of the present disclosure, such as interlaminar, lateral, and anterior approaches. One or more trial portions 28a-n of various sizes, such as the trial portions 28a and 28b depicted, can be inserted and removed as needed, preferably along the same approach axis 25 (i.e., such that the central axis 10 of the delivery body 4 is substantially aligned with the approach axis 25), to gauge the appropriate size of the disc space 7, such as the disc height, and optionally also an insertion depth to a target location or reference location within the disc space, such as the intersection of the coronal midline CM and the sagittal midline SM, by way of a non-limiting example. The at least one opening 14 and any markers of the delivery bodies 4a, 4b are viewed using lateral and/or frontal X-rays to confirm the appropriate position of the trial portion 28a-n within the disc space 7. The foregoing process can be repeated as needed with delivery bodies 4a-n having trail portions 28a-n of increasing or decreasing sizes, until a trail portion 28a-n having a satisfactory size is inserted within the disc space 7. In FIGS. 2A and 2B, trial portion 28b is shown as the exemplary trial portion 28 having such a satisfactory size for insertion within the disc space 7. It should be appreciated that the trial portion 28 having a satisfactory size may be one that distracts the vertebrae along the cranial-caudal direction C-C in the manner described above. It should also be appreciated that the satisfactory trial portion 28 can be inserted within the disc space with the assistance of a tool, such as by impacting the proximal surface 24 of the respective delivery body 4 with an impaction hammer. Moreover, the nose 31 of the trial portion 28 (and thus the nose 31 of the distal region 26 generally) can also be configured to receive impactions, such as from an impaction hammer, for fine controlled movement of the nose 31 within the disc space 7.

Once the trial portion 28a-n having a satisfactory size (e.g., maximum height H1) has been selected and inserted within the disc space 7, as visually assisted by the optical views described above, the carrier 50, with its channel 52 loaded with the biomaterial 9, can be inserted within the cannulation 12 of the delivery body 4 inserted within the disc space 7. Then, the push rod 73 can be driven distally within the central bore 58 and channel 52 of the carrier 50, and thus also within the cannulation 12 of the delivery body 4a-n, thereby expelling the biomaterial 9 from the cannulation 12, through the at least one opening 14, and into the disc space 7. If additional biomaterial 9 is desired in the disc space 7, the carrier 50 can be withdrawn from the cannulation, and a subsequent carrier 50 loaded with additional biomaterial 9 (or the same carrier 50 re-loaded with additional biomaterial 9) can be inserted in the cannulation 12, as before. The foregoing process can be repeated until the desired quantity of biomaterial 9 is delivered to the disc space. As shown in FIG. 2C, the delivery body 4 can be inserted through a retractor body, such as a retractor tube 500, that is supported by a spinal mounting assembly 600, as shown. The retractor tube 500 and spinal mounting assembly can be configured as more fully described in U.S. Patent Publication No. 2018/0008253 A1, published on Jan. 11, 2018, entitled "Multi-Shield Spinal Access System", the entire disclosure of which is incorporated by reference herein. With continued reference to FIG. 2C, the push rod 73 can be driven distally, at least in part, by impacting the impaction pad 80 of the force transmission member 78 with an impaction hammer 89. Additionally, from the optical views, in combination with the sizing of the one or more trial portions 28a-n, the size of a subsequent intervertebral fusion cage can be chosen.

It should be appreciated that the trial portions 28a-n can be used for more than simply ascertaining the disc height between vertebral bodies 3a, 3b. In particular, the trial portions 28a-n can be used to determine whether the desired position of the intervertebral fusion cage is reachable, whether enough disc material has been removed, and the like. It should also be appreciated that the instrument assemblies 2 described herein can also be employed to deliver the biomaterial 9 around or within a fusion cage that has been inserted within the disc space. For example, in a spinal fusion procedure, an instrument assembly 2 can be employed to deliver a first quantity of the biomaterial 9 into the disc space 7 and the assembly 2 can be withdrawn therefrom; a fusion cage, such as an expandable fusion cage, can then be inserted to a desired position within the disc space 7 and expanded, such as along the cranial-caudal C-C direction; and the instrument assembly 2, having the same or a different delivery body 4a-n (or second portion 4t thereof) as before can be inserted back into the disc space 7 and can deliver an additional quantity of the biomaterial 9 around and/or within the fusion cage.

Additional configurations of the distal region 26 of the delivery body 4 will now be described with reference to FIGS. 3 through 5B.

Figure 3:
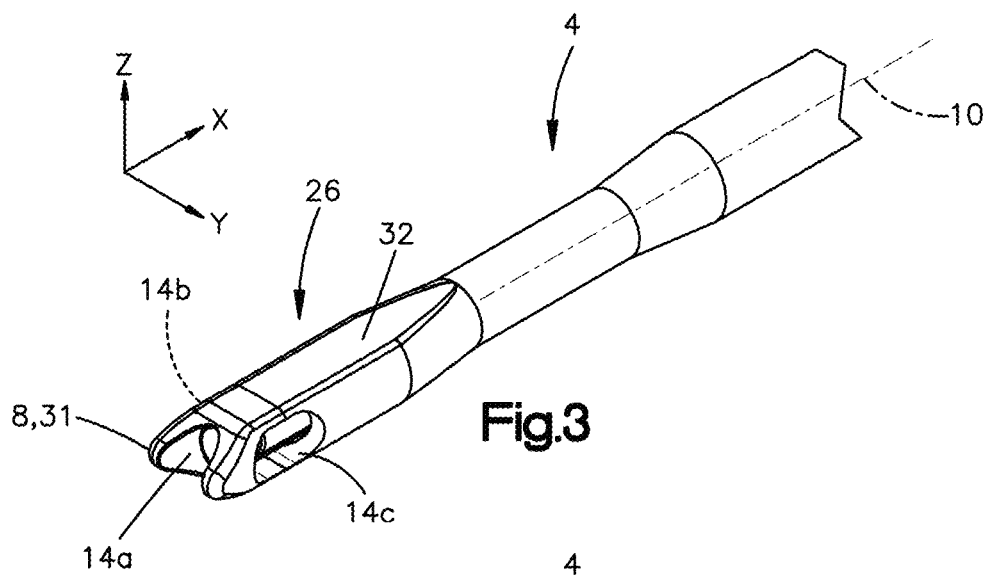
FIG. 3 is a perspective view of a distal region of the instrument assembly, having an axial opening and a pair of side openings, according to another embodiment of the present disclosure.

Referring now to FIG. 3, the delivery body 4 can be configured to expel the biomaterial 9 from one or more sides of the distal region 26, as well as axially therefrom. In particular, the at least one opening 14 at the distal region 26 can include an axial opening 14a at the distal end 8 and a pair of opposed side openings 14b, c spaced from each other along a third or lateral direction Y perpendicular to the longitudinal direction X and the second direction Z. In such embodiments, the distal region 26 can expel the biomaterial 9 distally, as well as laterally in opposite directions away from the central axis 10, from the delivery body 4 and into the disc space 7. As shown, the opposed side openings 14b, c can be proximally spaced from the axial opening 14a. In the present embodiment, the three openings 14a-c allow the biomaterial 9 to follow the path of least resistance from the delivery body 4 into the disc space, which can be particularly advantageous should one or two of the openings 14a-c be blocked or partially blocked, such as by disc material, such as an unremoved portion of the nucleus pulposus and/or anulus fibrosis. It is to be appreciated that the distal region 26 of the present embodiment can be otherwise substantially similar to the that of the embodiments illustrated in FIGS. 1E and 1F.

Figure 4A:
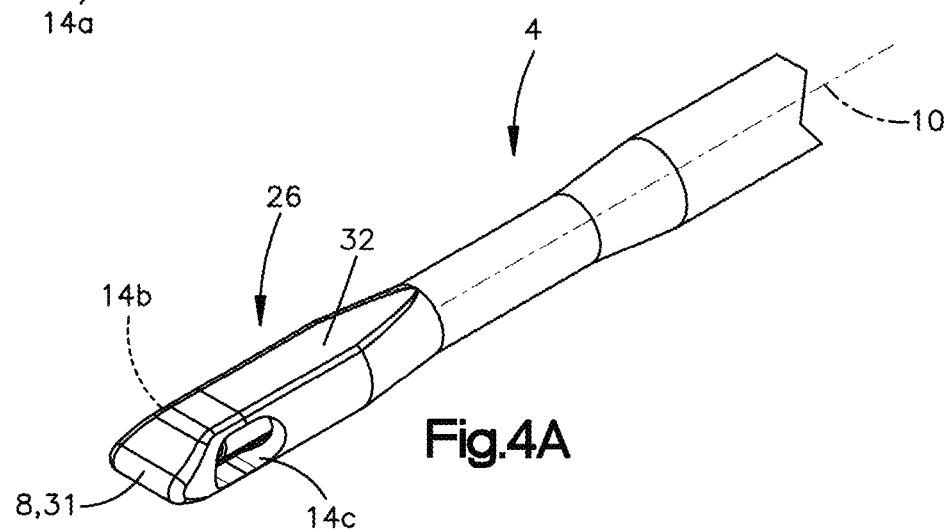
FIG. 4A is a perspective view of a distal region of the instrument assembly, having a pair of side openings, according to an additional embodiment of the present disclosure.
Figure 4B:
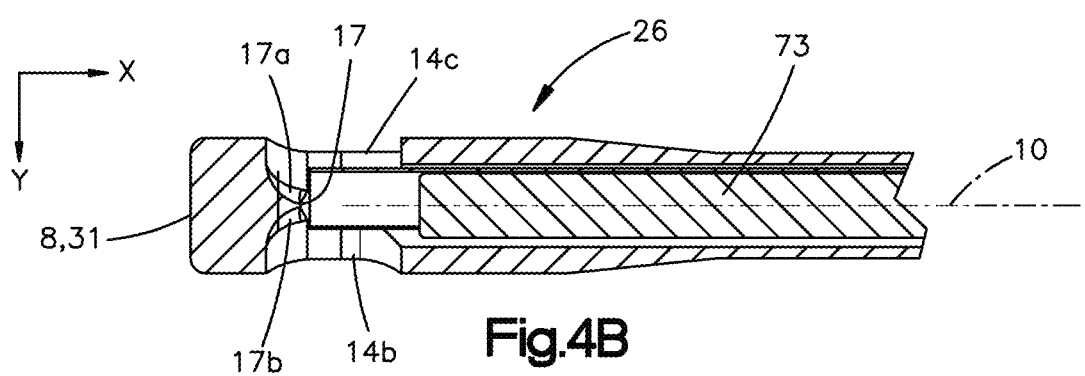
FIG. 4B is a top sectional view of the distal region of the instrument assembly illustrated in FIG. 4A.

Referring now to FIGS. 4A and 4B, in other embodiments, the delivery body 4 can be configured to expel the biomaterial 9 in opposite directions laterally away from, but not distally from, the distal region 26. In particular, in such embodiments, the least one opening 14 can include the pair of opposed side openings 14b, c without the axial opening 14a of the preceding embodiment, such that the distal end 8 of the delivery body 4 is closed in the longitudinal direction X. Additionally, the delivery body 4 can include a diversion formation, such as a wedge formation 17 at a terminal distal end of the cannulation 12. The wedge formation 17 can be aligned along the central axis 10 between the pair of side openings 14b, c and can have an apex that faces proximally, with a pair of side surfaces 17a, b that are configured to divert the biomaterial 9 from the cannulation 12 laterally out the pair of opposed side openings 14b, c. The side surfaces 17a, b of the wedge formation 17 can be arcuate, as shown, or can be straight in other embodiments. As above, it should be appreciated that the distal region 26 of the presently illustrated embodiment can be otherwise substantially similar to the distal regions 26 of the embodiments illustrated in FIGS. 1E and 1F and FIG. 3.

The delivery body 4 can optionally be constructed of a material allowing the body 4 to elastically deform radially outward from the central axis 10 as the biomaterial 9 is pushed distally through the cannulation 12. In this manner, the delivery body 4 can be constructed with smaller dimensions in the lateral and vertical directions Y, Z and can employ the foregoing flexibility to avoid biomaterial 9 blockages therein. Thus, the delivery body 4 constructed in this manner can have an overall less invasive instrument profile. In such embodiments, the delivery body 4 can include one or more support elements, such as support rods, which can be formed of steel, for example, and extend longitudinally along the delivery body 4 to maintain its structural integrity, such as to prevent, or at least substantially prevent, plastic deformation of the delivery body 4.

Figure 5A:
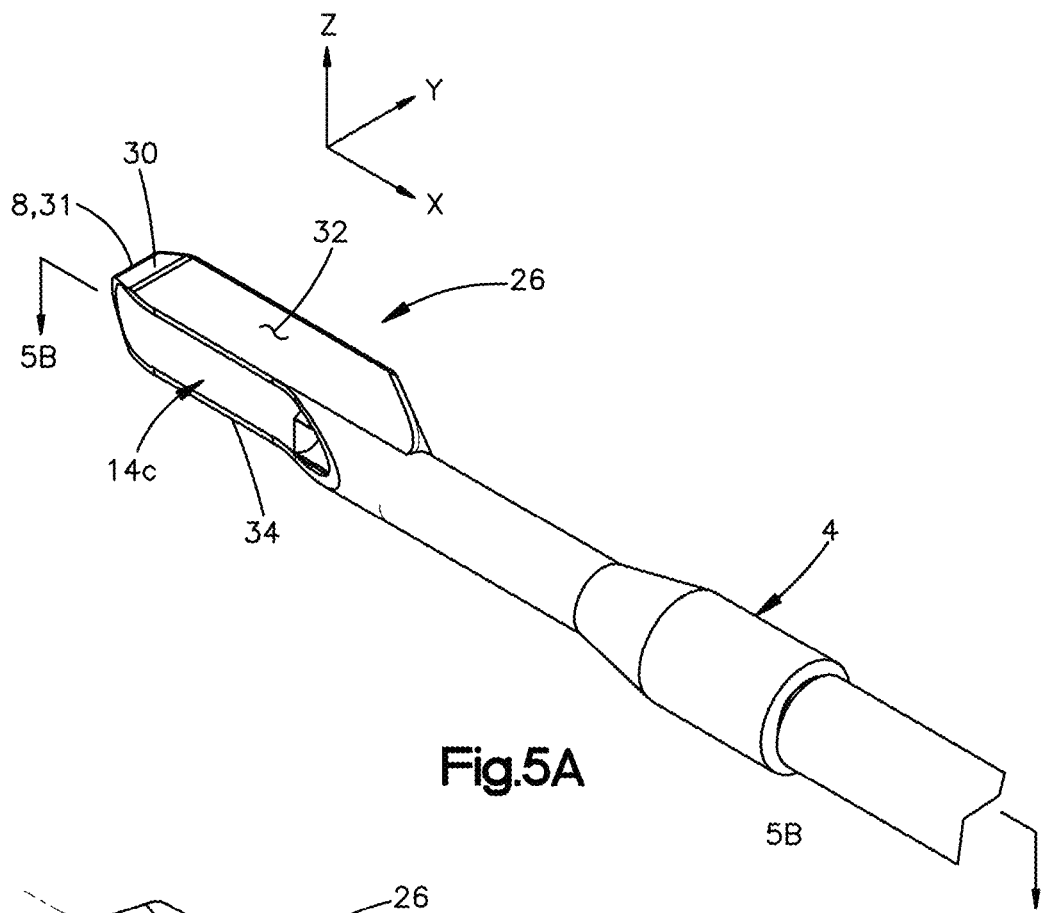
FIG. 5A is a perspective view of a distal region of the instrument assembly, having a single side opening, according to a further additional embodiment of the present disclosure.
Figure 5B:
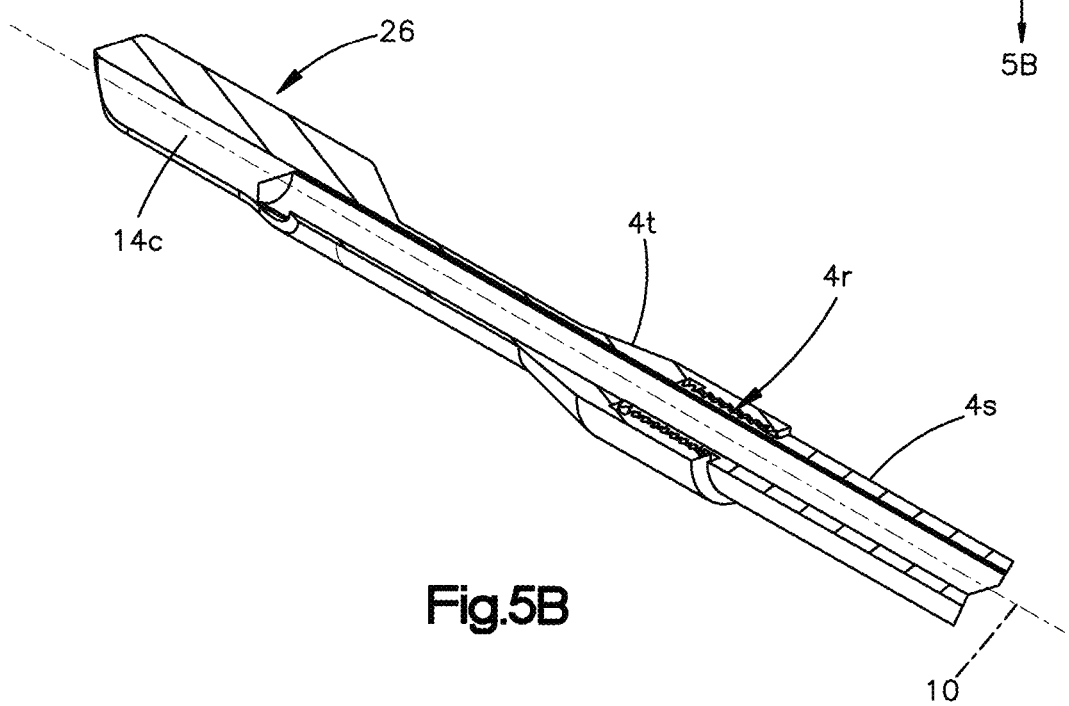
FIG. 5B is a sectional perspective view of the distal region of the instrument assembly illustrated in FIG. 5A.

Referring now to FIGS. 5A and 5B, the delivery body 4 can alternatively include a single side opening 14c that is open at least along the lateral direction Y. The single side opening 14c can also be elongate along, as well as open along, the longitudinal direction X. In such embodiments, the distal region 26 can optionally include a diversion formation for diverting the biomaterial 9 from the cannulation 12 and out the single side opening 14b laterally into the disc space. As above, the distal region 26 of the present embodiment can be otherwise similar to the distal regions 26 of the embodiments illustrated in FIGS. 1E and 1F; FIG. 3, and FIGS. 4A and 4B. For example, the distal region 26 can include a tip 30 that tapers distally to a rounded nose 31 at the distal end 8. Moreover, the distal region 26 can include first and second contact surfaces 32, 34 opposite each other along the second direction Z. The first and second contact surfaces 32, 34 of the present embodiment can be spaced from each other by the maximum height H2, measured along the second direction Z, as in the embodiments described above.

As shown in FIG. 5B, the delivery body 4 can also include a coupling 4r, such as a threaded coupling, for example, at which a first or proximal section 4s of the delivery body 4 couples with a separate second or distal section 4t of the delivery body 4. The proximal section 4s can include the mounting formation 18 and the distal section 4t can include the distal region 26 (and thus also the trail portion 28a-n). In this manner, the trial portions 28a-n of the delivery bodies 4a-n described above can be provided in a kit system 99 that includes a plurality of the distal sections 4t that are of different size and are interchangeable with a first section 4s via the coupling 4r. It should be appreciated that the delivery bodies 4 of other embodiments of the present disclosure can include interchangeable second sections 4t and first portions 4s.

Referring now to FIGS. 6A and 6B, in additional embodiments, the instrument assembly 2 can include additional instrumentation, such as a biomaterial retention mechanism 40, which can integral with the delivery body 4. For example, the biomaterial retention mechanism 40 can be a monolithic proximal extension of the delivery body 4. The biomaterial retention mechanism 40 is configured to retain loaded biomaterial 9 within the instrument assembly 2, including within the cannulation 12, while the carrier 50 is withdrawn proximally from the delivery body 4 and the biomaterial retention mechanism 40. In this manner, the carrier 50 can be removed from the cannulation 12 before the advancement member 70 is inserted, which frees up space within the cannulation 12 and can reduce friction between the biomaterial 9 and the delivery body 4. To accommodate the longitudinal length of the biomaterial retention mechanism 40, it should be appreciated that the carrier 50 and advancement member 70 for use in the present embodiment can have respective longitudinal lengths greater than those in the embodiments above. It should also be appreciated that the biomaterial retention mechanism 40 can be a separate component that is attachable to the delivery body 4. For example, a distal end 43 of the biomaterial retention mechanism 40 can be configured to couple to the proximal mounting formation 18 of the delivery body 4, such that the biomaterial retention mechanism 40 extends proximally from the delivery body 4. Additionally, the biomaterial retention mechanism 40 can be configured as an optional auxiliary instrument that can attach to and detach from the delivery body 4 as needed.

The biomaterial retention mechanism 40 can include a proximal end 41 spaced from the distal end 43 along the longitudinal direction X. The biomaterial retention mechanism 40 includes a switch, such as a latch 42, that includes an occlusion formation 44 having a shape complimentary with the shape of the carrier channel 52 in a reference plane RP1 orthogonal to the central axis 10. The latch 42 is configured to iterate between an open position (as shown in FIG. 6A), in which the occlusion formation 44 is remote from the channel 52, and a closed position (as shown in FIG. 6B), in which the occlusion formation 44 is positioned in the channel 52 proximally of at least some, and preferably a majority of, the biomaterial 9. The latch 42 can be coupled to the mounting formation 18 via a hinged connection 44, for example. During use, while the latch 42 is in the open position, the carrier 50 can be loaded with the biomaterial 9 and then fully inserted within the delivery body 4. With the carrier 50 fully inserted, or optionally less than fully inserted, the latch 42 can be moved to the closed position so that the occlusion formation 44 is positioned within the carrier channel 52 proximally of at least some of the biomaterial 9, and the carrier 50 can then be withdrawn proximally from the cannulation 12. In this manner, the occlusion formation 44 will retain the biomaterial 9 within the cannulation 12 distally of the occlusion formation 44. With the carrier 50 removed from the cannulation 12, clearance between the inner diameter D1 of the cannulation 12 and at least some, and up to a majority of, the biomaterial 9 is increased, which reduces friction between the biomaterial 9 and the instrument assembly 2 as the push rod 73 pushes the biomaterial 9 distally through the cannulation 12.

The occlusion formation 44 can include a tapered proximal surface 46 configured to allow the push rod 73 to push the occlusion formation 44 toward the open position and out of the channel 52. The occlusion formation 44 can also include a distal surface 48 that is configured to be substantially orthogonal to the central axis 10 when in the closed position, thus blocking proximal movement of the biomaterial 9 as the carrier 50 is proximally withdrawn from the cannulation 12. The latch 42 can also include an outer surface, such as a thumb pad 49, which is configured for manually operating the latch 42, such as to manually hold the latch 42 in the closed position, and/or iterate the latch 42 between the open and closed positions, as needed. It is to be appreciated that the latch 42 can optionally include a locking mechanism configured to maintain the latch 42 in the closed position. The latch 42 can optionally be biased, such as by a spring, into either the open position or the closed position.

Figure 7A:
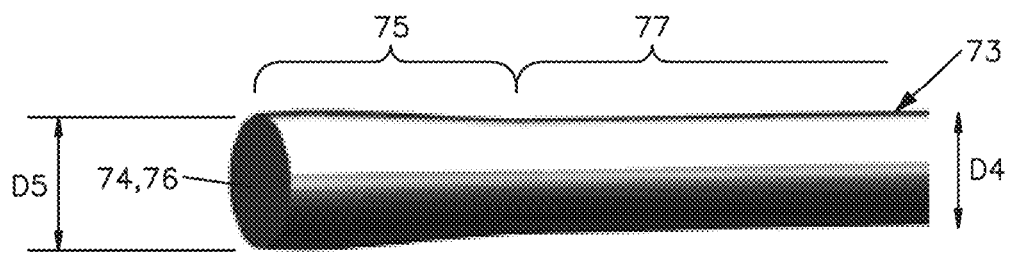
FIG. 7A is a perspective view of a variation of a distal end of an advancement member of the instrument assembly illustrated in FIG. 1A.

Referring now to FIGS. 7A through 7A, example alternative configurations of the distal end 74 of the push rod 73 will be described.

As shown in FIG. 7A, a distal region 75 of the push rod 73, which distal region 75 extends to the distal end 74 of the push rod 73, can define an outer diameter D5 that is greater than the outer diameter D4 of the push rod 73 at a proximal region 77 thereof, which proximal region 77 extends from the distal region 75 in the proximal direction XP. Additionally, the outer diameter D5 of the distal region 75 can be slightly greater than the inner dimeter D3 of the channel 52 of the carrier 50. In such embodiments, the thickness T1 of the carrier 50, as well as the material composition thereof, can be selected so that the distal region 75 of the push rod 73 causes elastic deformation of the carrier body 55 outwardly in the radial direction R as the distal region 75 travels longitudinally along the channel 52 to push the biomaterial 9. In this manner, the outward elastic deformation of the carrier body 55, particularly along the channel 52, reduces friction between the biomaterial 9 and the channel 52 as the biomaterial 9 is pushed distally therethrough. In such embodiments, the carrier 50 can optionally include one or more support elements, such as longitudinal support rods, which can be formed of steel, for example, and extend along the carrier 50 so as to prevent excessive deformation. The push rod 73 and carrier 50 constructed in accordance with the present embodiment can be employed with the elastically deformable delivery body 4 described above, or can alternatively be employed with a delivery body 4 configured to have a substantially rigid construction.

Figure 7B:
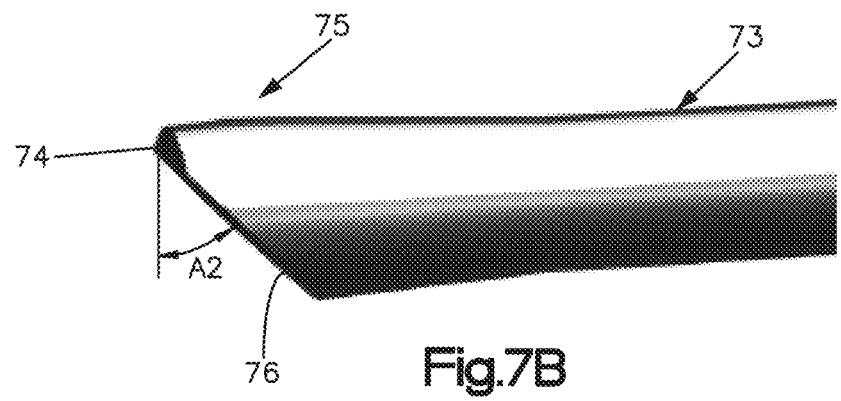
FIG. 7B is a perspective view of another variation of the distal end of the advancement member.

As shown in FIG. 7B, additionally or alternatively to the distal end 74 having an increased diameter D5, the distal surface 76 of the push rod 73 can be canted downwardly at an angle A2, particularly away from the elongate channel opening 53 when the push rod 73 is inserted within the channel 52. The distal surface 76 being canted in such a manner provides a measure of control over the force applied to the biomaterial 9, particularly by directing at least a portion of the force away from the elongate channel opening 53 to prevent, or at least reduce the potential for, the biomaterial 9 contacting the inner surface of the cannulation 12 proximally of the opening 14, and thereby avoiding friction therewith. Additionally or alternatively, the distal surface 76 can have a curved profile, such as domed profile or the like.

Figure 7C:
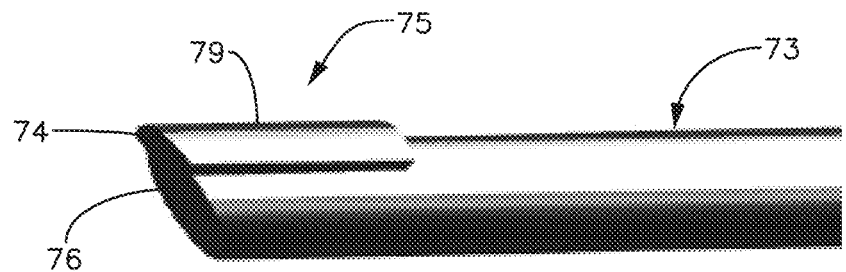
FIG. 7C is a perspective view of an additional variation of the distal end of the advancement member.

As shown in FIG. 7C, the distal region 75 of the push rod 73 can also include a formation, such as a partial circumferential boss 79, that is configured to reside within or otherwise occupy the elongate channel opening 53 in a manner preventing, or at least reducing instance of, the biomaterial 9 exiting through the elongate channel opening 53 and contacting the inner surface of the cannulation 12 proximally of the at least one opening 14. In this embodiment, the distal surface of the push rod 73 can also be canted, as described above.

Figure 7D:
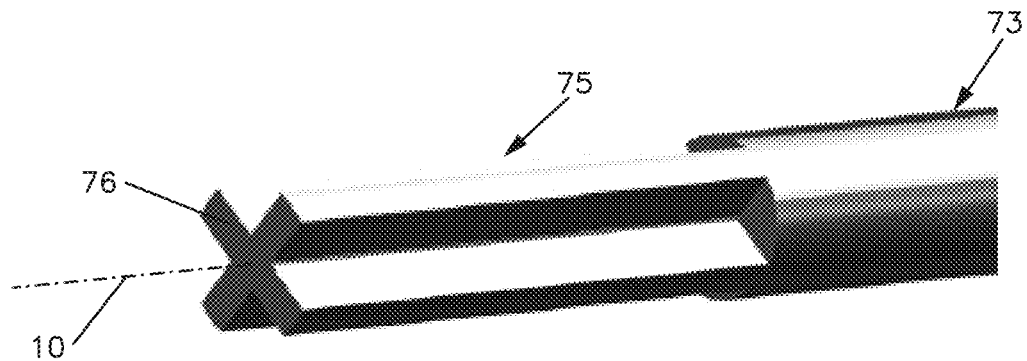
FIG. 7D is a perspective view of a further variation of the distal end of the advancement member.

As shown in FIG. 7D, the distal region 75 can additionally and/or alternatively be configured to reduce an initial contact force applied to a portion of the biomaterial 9. In such embodiments, the distal region 75 can have a geometry that defines a shape, such as cross-like shape, in a reference plane RP1 orthogonal to the central axis 10, thus also providing the distal surface 76 with a cross-like shape. The cross-like shape of the distal surface 76 can effectively impart the initial contact force to only a portion of the biomaterial 9, which can reduce the overall compression of the biomaterial 9, thus also reducing instances of the biomaterial 9 "sticking" to the interior surface of the channel 52 and/or contacting or sticking to the cannulation 12.

It is to be appreciated that, additionally and/or alternatively to any of the preceding embodiments, the push rod 73 can include a resilient member, such as a spring, located proximally of the distal end 74 and configured to provide a gradual increase in the axial force imparted to the biomaterial 9 by the distal surface 76.

Figure 8B:
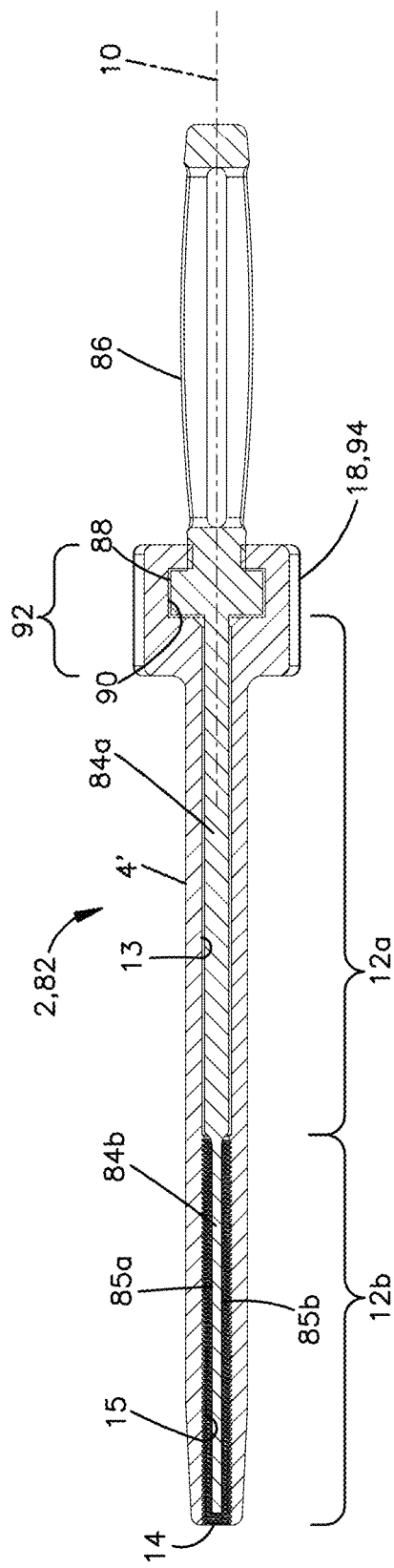
FIG. 8B is a sectional side view of the instrument assembly illustrated in FIG. 8A.
Figure 8C:
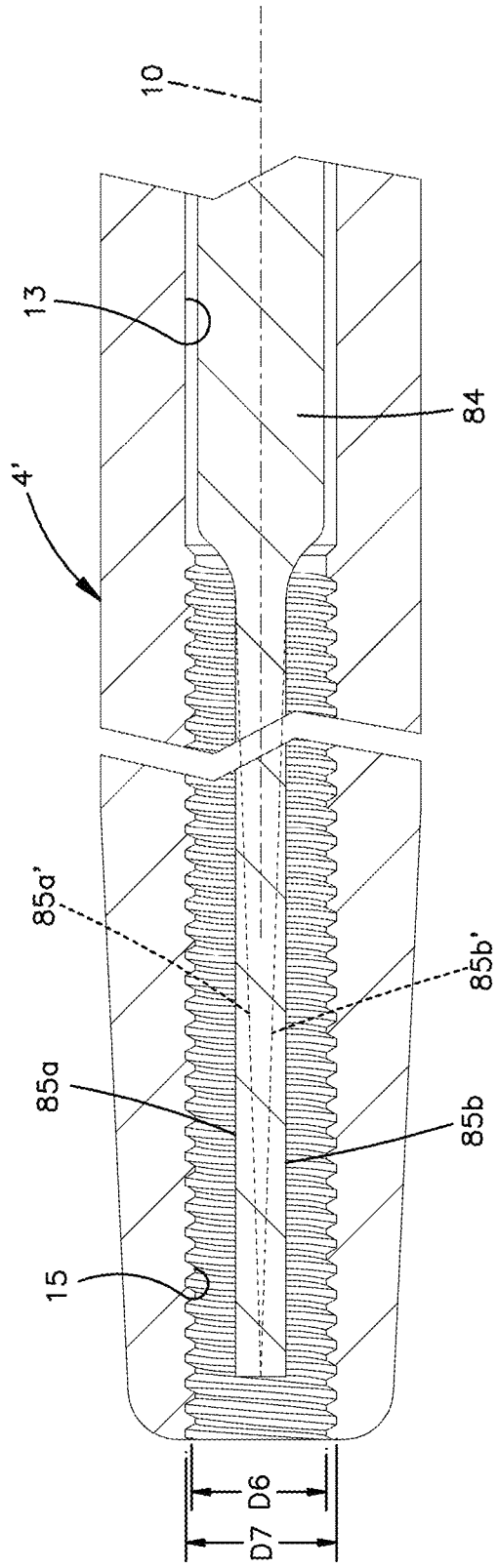
FIG. 8C is an enlarged sectional view of a distal portion of the instrument assembly illustrated in FIG. 8B.

Referring now to FIGS. 8A through 8C, in additional embodiments, the instrument assembly 2 can include an advancement member 70' that is configured to be mechanically controlled by an advancement mechanism, such as a rotary advancement mechanism 82, to advance the biomaterial 9 through a cannulated delivery body 4'. The rotary advancement mechanism 82 advantageously employs mechanical advantage to advance the biomaterial 9, as well as finer control over expulsion of the biomaterial 9 into the disc space. In the depicted embodiment, the biomaterial 9 can be packed within internal threads 15 of the cannulated delivery body 4' and effectively unthreaded therefrom and into the disc space, as described in more detail below.

The delivery body 4' can define a cannulation 12' that includes a proximal portion 12a having a substantially smooth inner surface 13 and a distal portion 12b that defines internal threads 15 extending helically about the central axis 10. Accordingly, the distal portion 12b can also be referred to as a "threaded" portion 12b of the delivery body 4'. The internal threads 15 define a minor thread diameter D6 and a major thread diameter D7. The minor thread diameter D6 of the delivery body 4' and the outer diameter D2 of the carrier 50 are cooperatively sized so that the carrier 50, loaded with biomaterial 9, can be inserted axially within the proximal portion 12a and into the threaded portion 12b, such that the biomaterial is radially inward from the minor thread diameter D6. From this position, a secondary loading instrument, such as a push rod, such as the push rod 73 shown in FIGS. 1B through 1D, by way of non-limiting examples, can be employed to expel the biomaterial 9 from the carrier channel 52 so that the biomaterial 9 resides in or adjacent to the threaded portion 12b of the cannulation 12'. In this manner, a satisfactory quantity of the biomaterial 9 can be loaded into or adjacent to the treaded portion 12b of the cannulation 12', which quantity can optionally include as much biomaterial 9 as can fit in the threaded portion 12b and also in at least an extent of the proximal portion 12a of the cannulation 12'. With the biomaterial 9 loaded in the cannulation 12', the biomaterial 9 can then be forced radially outward into the internal threads 15 of the cannulation 12' so that at least some of the biomaterial 9 resides radially between the minor and major thread diameters D6, D7, as described in more detail below. It should also be appreciated that the at least one opening 14 can be blocked or otherwise occluded while the biomaterial 9 is forced radially into the internal threads 15.

In the current embodiments, the advancement member 70' can include an elongate insertion member 84 configured for insertion within the cannulation 12', a proximal handle portion 86 coupled to the insertion member 84, and a mounting formation 88 disposed longitudinally between the handle portion 86 and the insertion member 84. The insertion member 84 can include a proximal insertion portion 84a configured to reside within the smooth proximal portion 12a of the cannulation 12' and a distal insertion portion 84b configured to reside within the threaded distal portion 12b of the cannulation 12' when the insertion member 84 is fully inserted within the delivery body 4'. The mounting formation 88 can be a radial flange or boss as shown, and is configured for mounting to a complimentary receiving formation 90 of the delivery body 4'. As shown, the receiving formation 90 can be a receptacle defined within the mounting formation 18 of the delivery body 4'. The mounting formation 88 and the receptacle 90 can be cylindrically shaped, and can cooperatively define a bearing mechanism 92 that can provide thrust bearing and journal bearing functionality. Accordingly, the bearing mechanism 92 can be referred to as a thrust bearing and/or a journal bearing. The bearing mechanism 92 can also effectively maintain the longitudinal position of the insertion member 84 within the cannulation 12' such that the proximal insertion portion 84a is aligned with the smooth proximal portion 12a and the distal insertion portion 84b is aligned with the threaded distal portion 12b of the cannulation 12'. In the presently depicted embodiment, the mounting formation 18 of the delivery body 4' can also define a grip member, such as a knob 94, configured to be manipulated by a physician for expelling the biomaterial 9 from the delivery body 4' and into the disc space. The knob 94 can include features, such as knurls and the like, for providing enhanced tactile manipulation of the knob 94, particularly for rotating the knob 94. It should be appreciated that the delivery body 4' can include an access feature, such as a latch, cover, or window or the like, that can be opened as needed for insertion and attachment of the mounting formation 88 within, and detachment from, the receiving formation 90.

The distal insertion portion 84b can define opposed first and second surfaces 85a, b spaced from each other along a radial direction R perpendicular to the central axis 10 (and thus also perpendicular to the longitudinal direction X). The opposed first and second surfaces 85 can each be substantially planar and provide the distal insertion portion 84b with a paddle-like geometry. As shown in FIG. 8A, the distal insertion portion 84b can also define opposed side surfaces 87a, b extending between the first and second surfaces 85a, b. The side surfaces 87a, b are spaced from each other by a radial distance that places the side surfaces 87a, b in close proximity to, or even in contact with, the minor diameter D6 of the threads 15. In use, once the biomaterial 9 has been forced into the internal threading 15 and the insertion member 84 is fully inserted within the cannulation 12', the bearing mechanism 92 allows the delivery body 4' to rotate relative to the advancement member 70', for example, by gripping the knob 94 and the handle portion 86 and rotating the knob 94 relative to the handle portion 86. As the delivery body 4' rotates relative to the advancement member 70', the opposed first and second surfaces 85a, b of the distal insertion portion 84b engage portions of the biomaterial 9 extending radially inward of the minor thread diameter D6 and force the biomaterial 9 to helically and distally advance along the internal threading 15 to the at least one opening 14 and therefrom into the disc space. In this manner, the biomaterial 9 is effectively "unthreaded" from the delivery body 4' into the disc space, such as in a corkscrew-like manner. The opposed first and second surfaces 85a, b substantially prevent the biomaterial 9 from rotating with the delivery body 4', thereby forcing the biomaterial 9 to advance helically along the internal threading 15 as the delivery body 4' rotates relative to the insertion member 84. It should be appreciated that, during use, the delivery body 4' and the insertion member 84 can be rotated relative to each other, or alternatively the insertion member 84 can be rotated relative to the delivery body 4', to drive the biomaterial 9 along the internal threads 15 and out the at least one opening 14. It should also be appreciated that the paddle-like geometry of the distal insertion portion 84b can optionally be used to push or otherwise force the biomaterial 9 radially into the internal threading 15. In additional embodiments, the first and second surfaces 85a, b can taper distally toward each other, as indicated by dashed lines 85a' and 85b' in FIG. 8C, so as to define a common edge at their distal ends. In this manner, the tapered first and second surfaces 85a', b' can push the biomaterial 9 outwardly into the internal threading 15 as the distal insertion portion 84b is inserted distally with the threaded distal portion 12b of the cannulation 12'.

It should be appreciated that any of the instrument assemblies 2 described above can also include additional features for reducing friction between the biomaterial 9 and components of the instrument assemblies 2, such as means for providing irrigation within the cannulation 12, 12'. Additionally or alternatively, internal surfaces of the cannulation 12, 12' and/or the channel 52 and central bore 58 of the carrier 50 can be coated or otherwise lubricated with one or more coating materials, such as hydrophobic coating materials or other lubricious materials. Additionally or alternatively, the biomaterial 9 can be pre-packaging or otherwise prepared with lubricious constituent material prior to loading within the carrier 50. Additional means for reducing friction are also within the scope of the present disclosure.

The following disclosure with reference to FIGS. 9A through 12D pertains to various examples of systems, assemblies, and devices for loading the biomaterial 9 into the carrier 50. Such systems, assemblies, and devices can be referred to herein as "loading systems", "loading assemblies," and "loading devices."

Figure 9A:
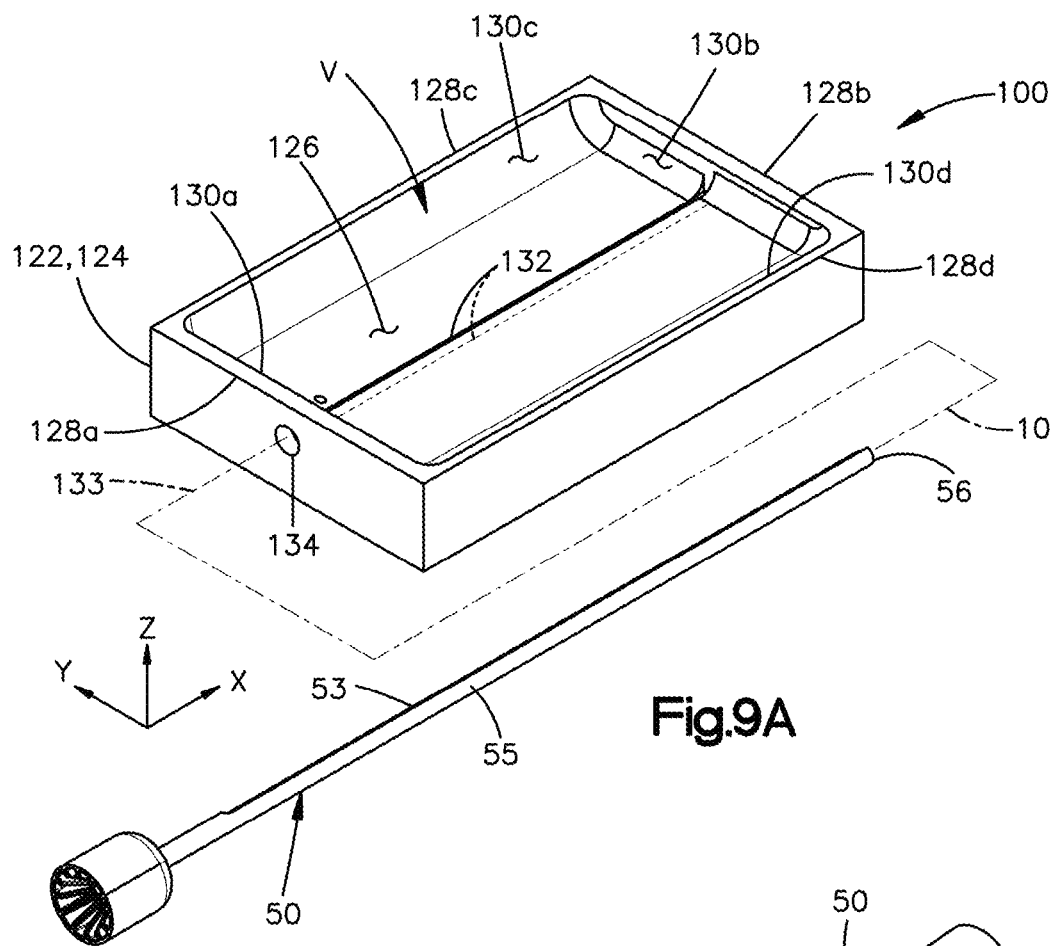
FIG. 9A is an exploded perspective view of a loading device for loading flowable biomaterial into a carrier of the instrument assembly illustrated in FIG. 1A, according to an embodiment of the present disclosure.
Figure 9B:
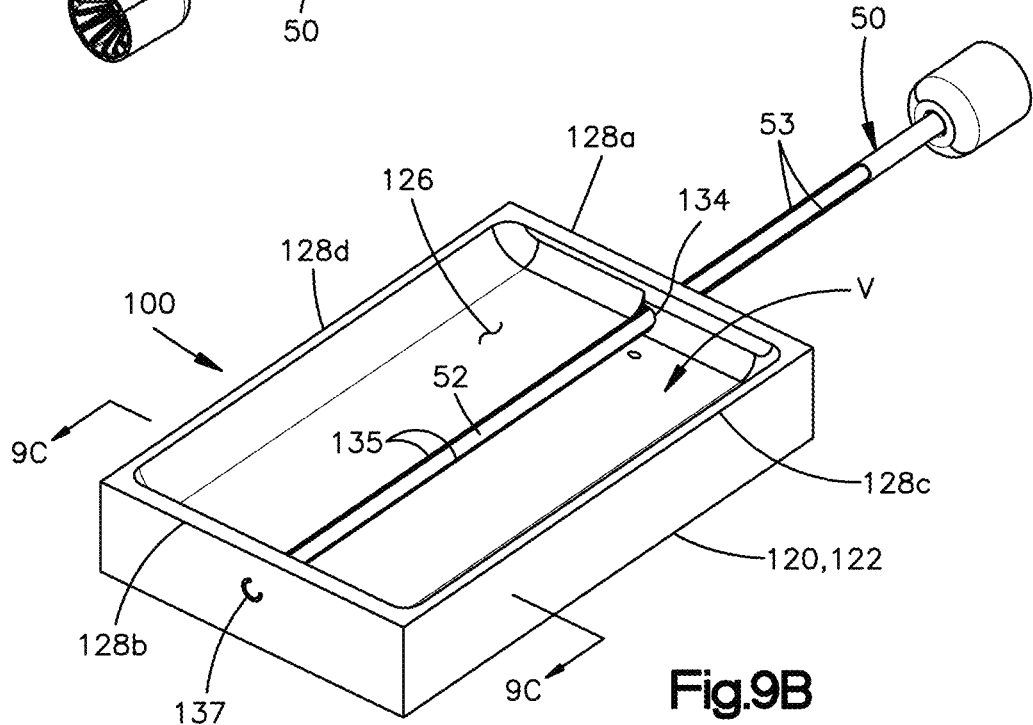
FIG. 9B is another perspective view of the loading device illustrated in FIG. 9A.

Referring now to FIGS. 9A and 9B, a loading system 100 includes a loading device 120 and can include one or more carriers 50. In the present embodiment, the loading device 120 includes a loading tray 122 having a tray body 124 that defines a floor surface 126 and sidewalls 128a-d extending upwards from the floor surface 126 along a vertical direction Z. The sidewalls 128a-n define interior wall surfaces 130a-n that, together with the floor surface 126, define a volume V of space for receiving biomaterial 9 to be loaded into the channel 52 of the carrier 50. The volume V of space can also be referred to as the "tray volume" V or simply the "volume" V. As shown, the tray 122 can be rectangular and can have four sidewalls 128a-d successively arranged at right angles to one another about the periphery of the floor surface 126. In particular, the tray 122 can have a first sidewall 128a and a second sidewall 228b opposite each other along the longitudinal direction X, and a third sidewall 228c and a fourth sidewall 128d opposite each other along the lateral direction Y.

The tray body 124 can define at least one elongate slot 132 that is recessed from the floor surface 126 and is open to, and thus in communication with, the volume V. The at least one elongate slot 132 is configured to receive at least a portion of the carrier 50, such as the elongate body portion 55 having the channel 52. The slot 132 defines a central slot axis 133 configured to be substantially coextensive with the central axis 10 of the carrier 50. Thus, the slot 132 can be characterized as being elongate along the longitudinal direction X. The slot 132 can extend from one of the sidewalls, such as the first sidewall 128*a*, to the opposite sidewall, such as the second sidewall 128*b*, in a manner intersecting the first and second sidewalls 128*a, b*. The slot 132 can also be in communication with an access opening or port 134 in one of the first and second sidewalls 128*a, b* for providing the carrier 50 with axial access to the slot 132 from an exterior of the tray 122. The slot 132 is at least partially defined by an elongate slot opening 135 contiguous with the floor surface 126. One or more and up to all of the interior wall surfaces 130*a-d* can be sloped inwardly toward the floor surface 126, such as to facilitate directing the biomaterial 9 deposited on the tray 122 toward the slot 132. As shown, the interior wall surfaces 130*a-d* can slope arcuately toward the floor surface 126. It is to be appreciated that, during use, the biomaterial 9 can be deposited within the volume V, such as generally on the floor surface 126 and/or directly over the slot 132.

As shown in FIG. 9B, to maintain the carrier 50 within the slot 132 so that the carrier channel 52 remains open to the volume V, the first or second sidewall 128*a, b* opposite the access port 134 can define a carrier retention receptacle 137 in axial communication with the slot 132 for receiving the distal end 56 of the carrier 50. The receptacle 137 has a receptacle profile in a reference plane orthogonal to the longitudinal direction X. The receptacle profile is complimentary with the trough-shaped profile of the distal end 56 of the carrier 50 in the reference plane, such that the carrier 50 is retained in the slot 132 at an orientation whereby the elongate channel opening 53 is open to the volume V.

Figure 9C:
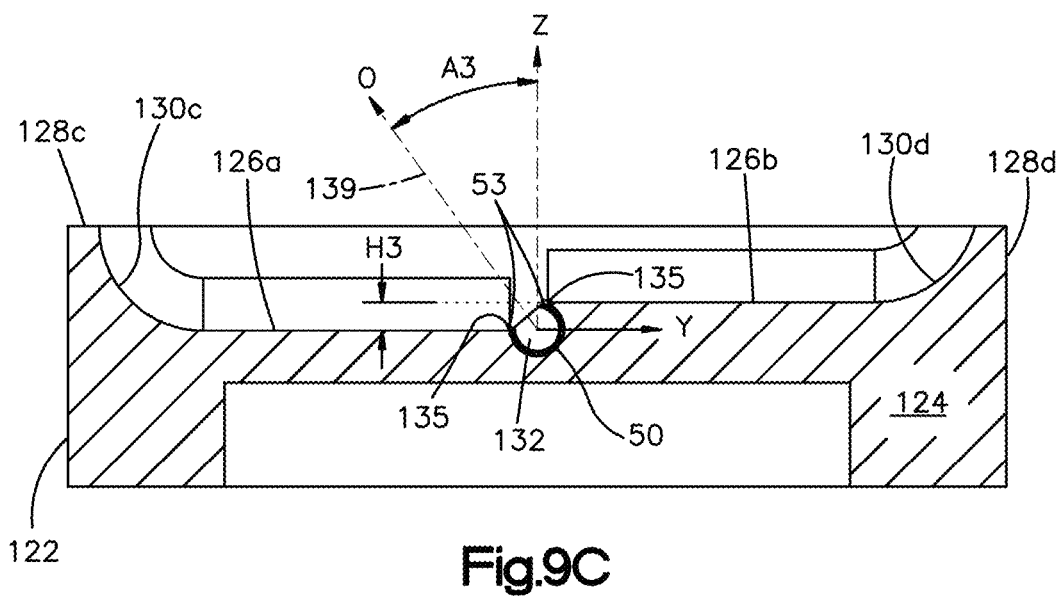
FIG. 9C is a sectional end view of the loading device taken along section line 9C-9C in FIG. 9B.

Referring now to FIG. 9C, the slot 132 is open to the volume V at least along a slot opening direction O that is oriented along a slot opening axis 139, which intersects and extends perpendicularly from the central slot axis 133 (and is thus perpendicular to the longitudinal direction X) and extends equidistantly between the edges of the elongate slot opening 135. The slot opening axis 139, and thus the slot opening direction O, are preferably offset from the vertical direction Z by an acute slot opening angle A3 in a range of about 0.5 degrees to about 90 degrees, and more particularly in a range of about 15 degrees to about 45 degrees, and preferably in a range of about 25 degrees to about 35 degrees, as measured from a vertical axis (i.e., an axis oriented along the vertical direction Z) that intersects the slot axis 133. Alternatively, the slot opening direction O can be aligned with the vertical direction Z. When the carrier 50 is inserted in the slot 132, the carrier retention receptacles 137 can maintain the carrier 50 so that the channel 52 is also open to the volume V along the slot opening direction O.

Additionally, the floor surface 126 of the tray 122 can include a first floor surface portion 126*a* on one side of the slot 132 and a second floor surface portion 126*b* on an opposite side of the slot 132. The first and second floor surface portions 126*a, b* can each extend to, and be contiguous with, the elongate slot opening 135. The first and second floor surface portions 126*a, b* can be offset from one another by an offset distance H3 along the vertical direction Z, which offset distance H3 can provide the slot opening angle A3. The carrier retention receptacle 137, the offset distance H3, and the slot opening angle A3 are preferably cooperatively configured to cause the edges of the elongate channel opening 53 to be substantially aligned with the edges of the elongate slot opening 135, thereby preventing the biomaterial 9 from impinging against the outer surface 51 of the elongate body portion 55 as the biomaterial 9 is moved to the channel 52. As shown, the second floor surface portion 126*b* can be elevated above the first floor surface portion 126*a* with respect to the vertical direction Z in step-like or terrace-like fashion. This step-like floor configuration facilitates moving the biomaterial 9 from the floor surface 126 into the carrier channel 52 loaded in the slot 132, particularly by pushing, scraping, and/or wiping the biomaterial 9 from the first floor surface portion 126*a* into the slot 132. Additionally, as shown, the second floor surface portion 126*b* can overhang a portion of the slot 132 for further directing the biomaterial 9 into the slot 132 as the biomaterial 9 is pushed, scraped, and/or wiped from the first floor surface portion 126*a* and into the slot 132.

It is to be appreciated that the tray body 124 can define a plurality of elongate slots 132 for receiving a plurality of carriers 50 to be loaded with biomaterial 9. For example, the tray body 124 can include two (2), three (3), four (4), five (5), or more than five (5) slots 132, each for receiving a respective carrier 50 therein. In such embodiments, the tray 122 can be configured to load one or more and up to each of the plurality of carriers 50 with biomaterial 9, as needed. Moreover, in such embodiments, the floor surface 126 can define a plurality of floor surface portions vertically offset from one another in step- or terrace-like fashion on opposite sides of each of the slots 132, for facilitating moving the biomaterial 9 from the floor surface portions into the slots 132, as described above. Additionally, the tray body 124 can also include a respective plurality of access ports 134 and/or carrier retention receptacles 137 in communication with the plurality of slots 132.

Figure 9D:
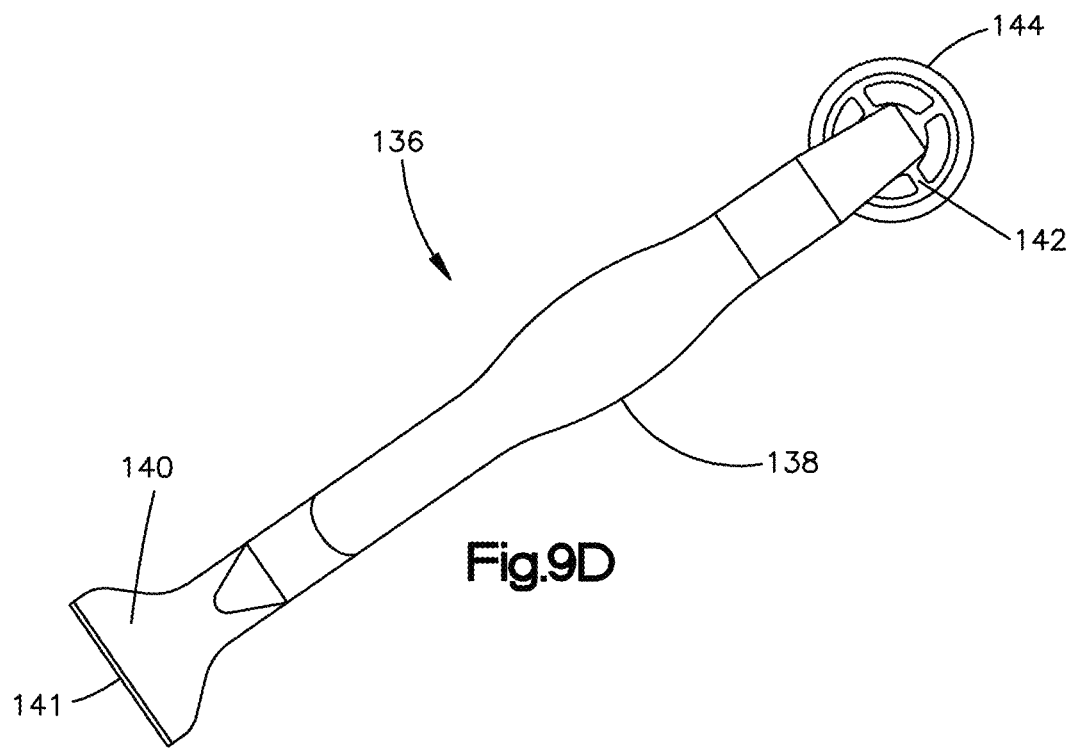
FIG. 9D is a perspective view of an auxiliary loading tool for use with the loading device shown in FIGS. 9A through 9C, according to an embodiment of the present disclosure.

Referring now to FIG. 9D, the loading system can include an auxiliary tool 136 for moving biomaterial 9 from the volume V of the tray 122 into the carrier channel 52 inserted within the slot 132. The auxiliary tool 136 of the present embodiment is configured to be manually manipulated for depositing the biomaterial 9 within the carrier channel 52 inserted within the slot 132. In particular, the auxiliary tool 136 can include a handle 138 and a push member, such as a wiper or scraper 140, extending from the handle 138. As shown, the scraper 140 can be a blade having a scraping edge 141. The scraper 140 is configured to deposit biomaterial into the carrier channel 52, such as by scraping, wiping, or pushing biomaterial 9 with the scraping edge 141 across the floor surface 126 and into the channel 52 residing in the slot 132. The scraper 140 is preferably comprised of a flexible material having a low hardness, as measured by a durometer, including rubber, silicone, or the like, by way of non-limiting examples, which flexible material provides the scraper 140 with flexibility, which is advantageous for scraping biomaterial 9 into the carrier channel 52. The auxiliary tool 136 can also include a tamp feature 142 extending from the handle 138 opposite the scraper 140. The tamp feature 142 is configured to tamp or press biomaterial 9 that has been scraped or otherwise loaded in the carrier channel 52, such as to cause the loaded biomaterial 9 to reside substantially entirely within the channel 52, so as to not extend radially outward of the elongate channel opening 53. As shown, the tamp feature 142 can be a wheel or roller having a contact surface 144 formed of a flexible material, such as rubber, silicone, or the like. The contact surface 144 of the wheel 142 can have a width greater than, substantially equivalent to, or slightly less than a lateral width of the elongate channel opening 53. In other embodiments, the auxiliary tool 136 can be a card-like member defining a scraping edge. It is to be appreciated that other configurations of the auxiliary tool 136 are within the scope of the present disclosure.

Figure 10A:
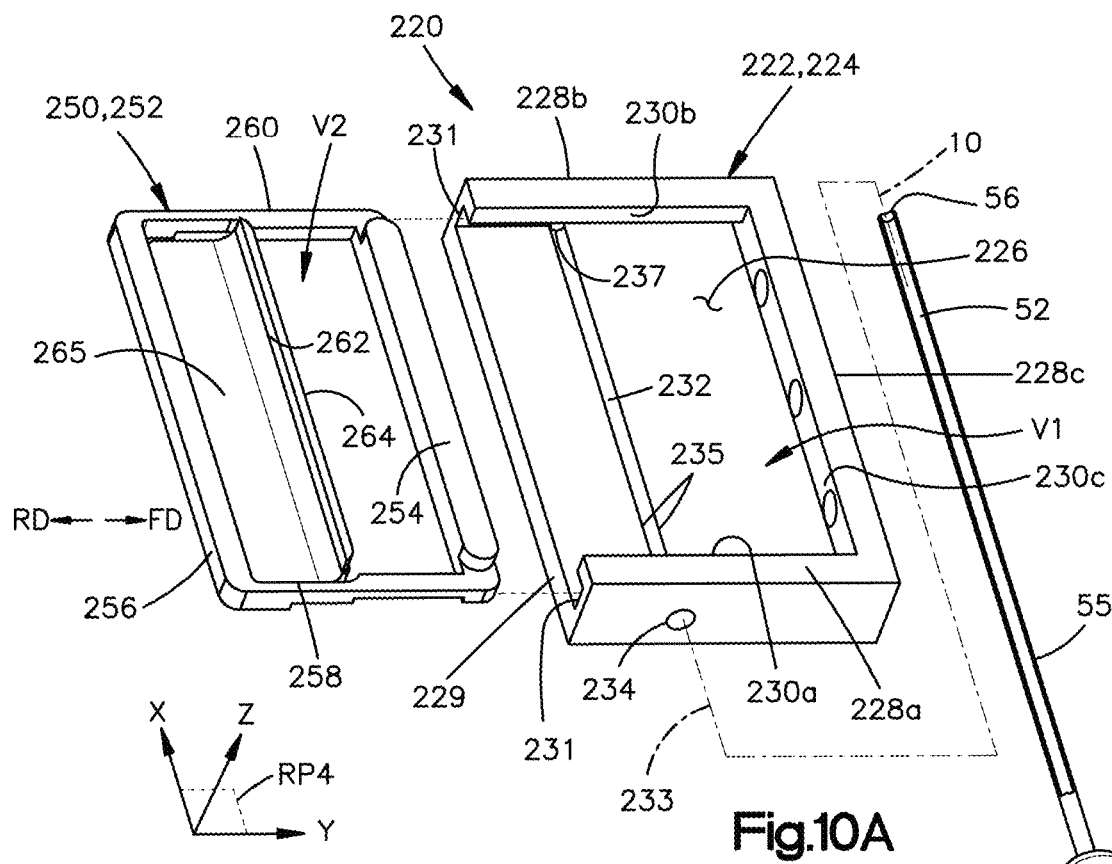
FIG. 10A is an exploded perspective view of another loading device for loading flowable biomaterial into the carrier of the instrument assembly illustrated in FIG. 1A, according to another embodiment of the present disclosure.
Figure 10B:
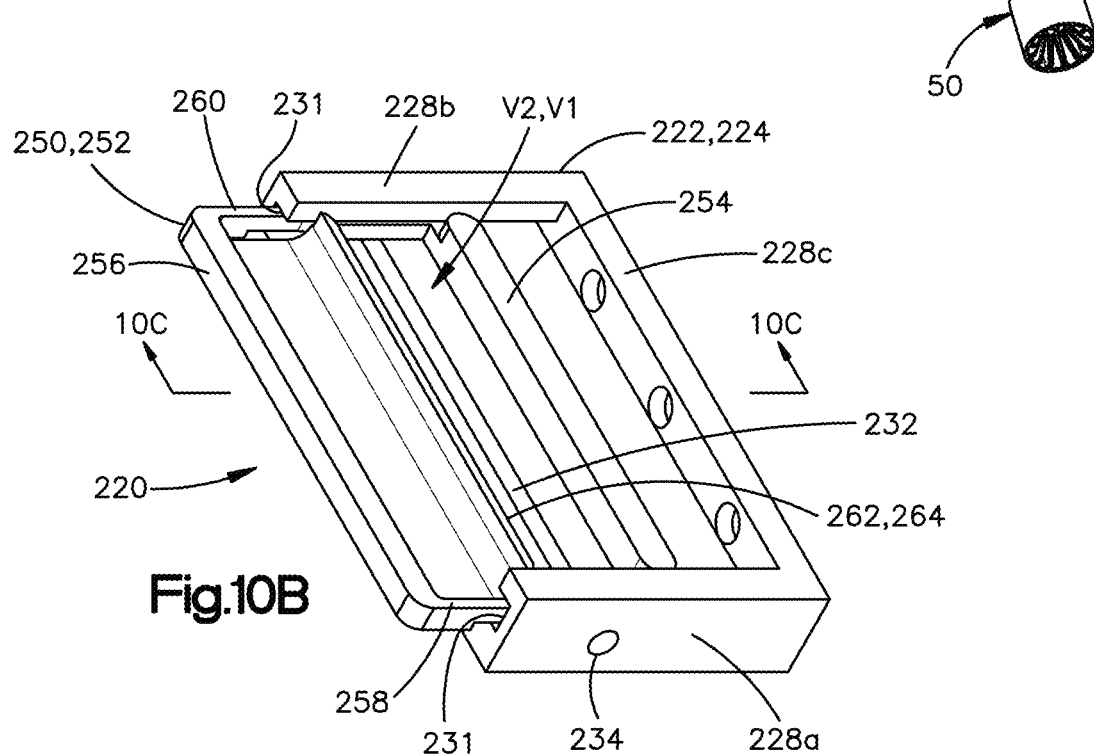
FIG. 10B is a perspective view of the loading device illustrated in FIG. 10A.

Referring now to FIGS. 10A and 10B, in other embodiments, a loading device 220 can include a loading tray 222 having at least one slot 232 and a moving mechanism 250 for pushing, scraping, and/or wiping biomaterial 9 deposited on the tray 222 into the at least one slot 232. As above, the at least one slot 232 is configured to receive the elongate body portion 55 of the carrier 50 for loading the biomaterial 9 into the carrier channel 52. The tray 222 can define a tray body 224 that defines a floor surface 226 and a plurality of sidewalls 228a-c extending vertically from the floor surface 226. The sidewalls 228a-c define respective inner surfaces 230a-c that, together with the floor surface 226, cooperatively define a first or primary volume V1 of space for receiving biomaterial 9. The primary volume V1 can also be referred to as the "tray volume" V1. In the present embodiment, the sidewalls 228a-c can include a first sidewall 228a, a second sidewall 228b opposite the first sidewall 228a along the longitudinal direction X, and a third sidewall 228c extending from the first sidewall to the second sidewall 228b along the longitudinal direction X. In the present embodiment, the tray body 224 can define an open end 229 opposite the third sidewall 228c with respect to the lateral direction Y. The open end 229 is configured to receive the moving mechanism 250.

The at least one elongate slot 232 can be recessed from the floor surface 226 and in communication with the tray volume V1. The slot 232 is elongate along a slot axis 233 that is oriented along the longitudinal direction X and is configured to receive the elongate body portion 55 of the carrier 50, particularly along the longitudinal direction X, similarly as described above. The slot 232 is at least partially defined by an elongate slot opening 235 contiguous with the floor surface 226. Additionally, as described above, the at least one slot 232 can be in communication with at least one corresponding access opening or port 234 defined in one of the sidewalls 228a-c for providing the carrier 50 with internal access to the slot 232. The at least one port 234 is preferably defined in the first or second sidewall 228a, b. The tray body 224 also preferably defines a carrier retention receptacle 237 in the other of the first or second sidewall 228a, b for receiving the distal end 56 of the carrier 50 and retaining the carrier 50 in the slot 232 so that the carrier channel 52 remains open to the tray volume V1, similarly as described above with reference to FIGS. 9A through 9C.

The moving mechanism 250 can include a slider body 252, at least a part of which, and up to an entirety of, is configured to move within the tray volume V1, such as by sliding across the floor surface 226. Thus, the slider body 252 can be referred to as a "slide member". In the illustrated embodiment, the slider body 252 is configured to slide relative to the tray body 224 in a forward direction FD toward first sidewall 228a of the tray body 224 and in a rearward direction RD away from the first sidewall 228a and opposite the forward direction FD. It is to be appreciated that, in the present embodiment, the forward and rearward directions FD, RD each extend along the lateral direction Y. The slider body 252 preferably has a shape, as viewed in a horizontal reference plane RP4 extending along the longitudinal and lateral directions X, Y, that generally corresponds to the shape of the floor surface 226 in a respective horizontal reference plane RP4. For example, as shown, the floor surface 226 and the slider body 252 can each have a generally rectangular shape in the horizontal reference plane RP4. The slider body 252 can define first and second slider endwalls 254, 256 opposite each other along the lateral direction Y. The slider body 252 can also define first and second slider sidewalls 258, 260 opposite each other along the longitudinal direction X and extending from the first slider endwall 254 to the second slider endwall 256. The slider endwalls 254, 256 and slider sidewalls 258, 260 can be substantially rigidly connected to one another. The inner surfaces 230a, b of the first and second tray sidewalls 228a, b can define guide features, such as guide channels 231, for receiving and guiding sliding movement of the slider sidewalls 258, 260 along the lateral direction Y. The first slider endwall 254 is configured to move within the tray volume V1. The second slider endwall 256 is configured to be manipulated, such as manually, so as to cause the first slider endwall 254 to move within the tray volume 1. Accordingly, the second slider endwall 256 can be referred to as a "handle wall" or simply as a "handle."

The slider body 252 includes a push member, such as a push wall 262, having a front surface 264 that is configured to face the third tray sidewall 228c and push biomaterial 9 deposited across the floor surface 226 toward, and into, the slot 232. As shown, the push wall 262 can be located between the first and second slider endwalls 254, 256 with respect to the lateral direction Y. The push wall 262 can be connected to the second slider endwall 256 by an extension member 265, which can be compliant, as described in more detail below. The slider body 252 is open between the push wall 262 and the first slider endwall 254 along the lateral direction Y so as to define a secondary volume V2 for receiving the biomaterial 9. The slider body 252 is configured to slide into the tray body 224 so that the secondary volume V2 is located within the tray volume V1.

Figure 10C:
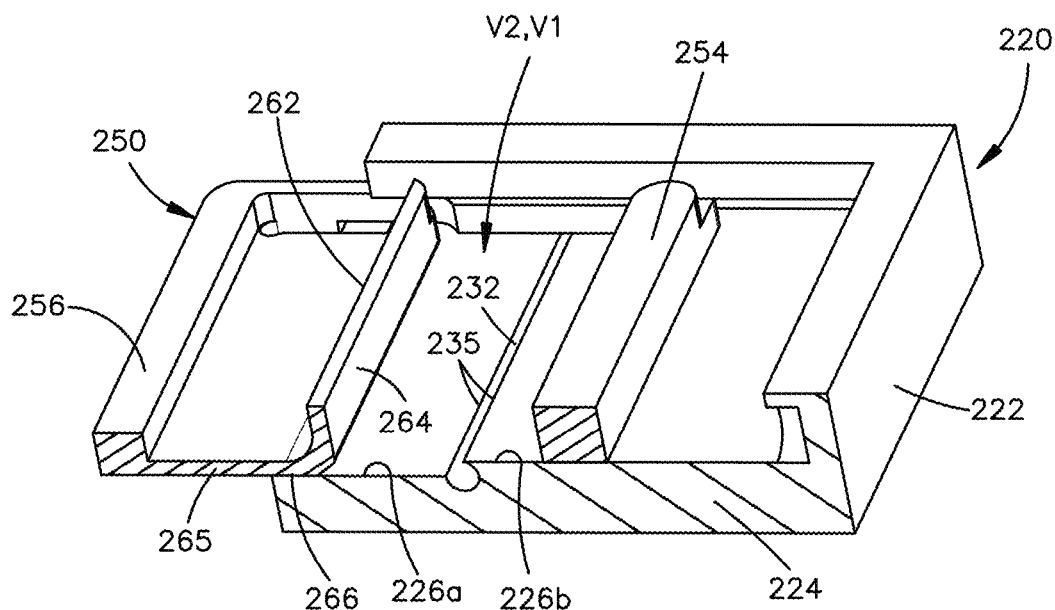
FIG. 10C is a sectional perspective view of the loading device, taken along section line 10C-10C in FIG. 10B.
Figure 10D:
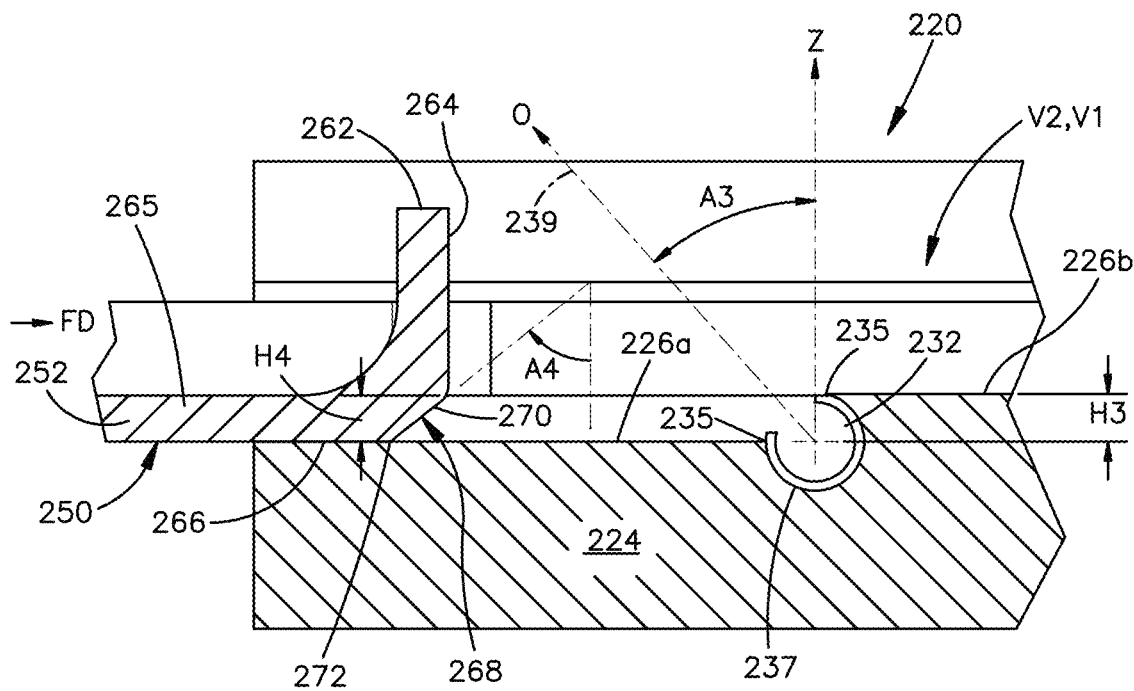
FIG. 10D is an enlarged sectional side view of a portion of the loading device illustrated in FIG. 10C.

Referring now to FIGS. 10C and 10D, the push wall 262 has a bottom surface 266 that can be configured to iterate between a neutral orientation (as shown) and a deflected or flexed orientation. The bottom surface 266 has a geometry that, when in the neutral orientation, preferably is complimentary with a geometry of the floor surface 226. For example, in the neutral orientation, the bottom surface 266 can be planar and parallel with the floor surface 226. The push wall 262 can also include a wiper 268 configured to direct at least some of the biomaterial 9 from the secondary volume V2 into the slot 232, and thus into any carrier channel 52 loaded in the slot 232. The wiper 268 can abut, or at least be in close proximity to, the floor surface 226, and can thus be configured to wipe, push, or otherwise direct biomaterial 9 from the secondary volume V2 (and thus also from the tray volume V1) into the slot 232. As shown, the wiper 268 can include a lower push surface 270, which can be contiguous or adjacent with the front surface 264 of the push wall 262. The push surface 270 can be oriented at a back rake angle A4, as measured from a vertical axis. The back rake angle A4 can be configured for, among other things, directing biomaterial 9 more directly into the slot 232, such as downward at an angle into the slot 232. The back rake angle A4 can be in a range of about 1 degree to about 75 degrees. In additional embodiments, the back rake angle A4 can be in a range of about 20 degrees and about 60 degrees. In further embodiments, the back rake angle A4 can in a range of about 40 degree to about 55 degrees. The push surface 270 can extend rearwardly to a rear edge 272, which can define a boundary or interface between the push surface 270 and the bottom surface 266 of the push wall 262.

The floor surface 226 can include first and second floor surface portions 226a, b on opposite sides of the slot 232 and vertically offset relative to each other in step- or terrace-like fashion, similarly to the manner described above with reference to FIG. 9C. As shown in FIG. 10D, one of the floor surface portions, such as the second floor surface portion 226b, can be elevated with respect to the other floor surface portion, such as the first floor surface portion 226a, by a vertical offset distance H3. In such embodiment, the push surface 270 of the wiper 268 can define a vertical dimension H4 that is equivalent to or greater than the vertical offset distance H3. The compliant extension member 265, in cooperation with the vertical dimension H4 and the back rake angle A4 of the push surface 270, can be configured to allow the push wall 262, as well as the push surface 270, rear edge 272, and bottom surface 266 thereof, to deflect vertically upwards to the deflected orientation as the push wall 262 traverses the slot 232 in the forward direction FD. Such deflection, allowing the push surface 270 and rear edge 272 to traverse and move beyond the slot 232 in the forward direction FD, enhances the loading of biomaterial 9 within the slot 232. The foregoing action can also beneficially push, wipe, scrape or otherwise move excess biomaterial 9 in the forward direction FD away from the carrier channel 52 disposed within the slot 232, such that the biomaterial 9 loaded in the carrier channel 52 does not extend radially outward beyond the elongate channel opening 53. Otherwise, such excess biomaterial 9 might impinge against the first tray sidewall 228a or edges of the port 234 and inadvertently be expelled from the channel 52 as the elongate body portion 55 is withdrawn from the slot 232 after loading. The compliant extension member 265 also allows the push wall 262 to deflect downwards to the neutral orientation as the push wall 262 returns across the slot 232 in the rearward direction RD, which rearward movement can further push excess biomaterial 9 from the channel 52. Moreover, the elevated floor surface portion, such as the second floor surface portion 226b in the depicted embodiment, can overhang a portion of the slot 232 for further directing the biomaterial 9 into the slot 232 as the push wall 262 moves in the forward direction FD.

Similar to the manner described above with reference to FIG. 9C, the slot 232 of the present embodiment is open to, and thus in communication with, the primary and secondary volumes V1, V2, at least along the opening direction O, which is oriented along a slot opening axis 239. As shown, the opening direction O can be offset from the vertical direction Z by the acute slot opening angle A3 described above. Alternatively, the slot opening direction O can be aligned with the vertical direction Z. As above, the slot 232 is preferably configured to retain the carrier 50 therein, such as with the carrier retention receptacle 237, so that the carrier channel 52 is also maintained open to the volumes V1, V2 along the opening direction O. Additionally, in embodiments employing the acute slot opening angle A3, it should be appreciated that the carrier retention receptacle 237, the offset distance H3, and the slot opening angle A3 are preferably cooperatively configured to cause the edges of the elongate channel opening 53 to be substantially aligned with the edges of the elongate slot opening 235, as described above.

An example method of using the loading device 220 can include inserting the carrier 50 into the slot 232 so that the carrier channel 52 is open to the tray volume V1. A quantity of material 9 can be deposited within the secondary volume V2 and onto the floor surface 226, such as onto the first floor surface portion 226a thereof, before or after the carrier 50 is inserted within the slot 232. With the carrier 50 disposed in the slot 232 and the channel 52 open along the opening direction O (or at least open to the volumes V1, V2), the slider body 252 can be slid in the forward direction FD across the floor surface 226 so that the push member 262 pushes biomaterial 9 downwardly into the slot 232, thereby loading at least some of the deposited biomaterial 9 into the slot 232. Moreover, the push member 262 can be advanced forward so as to entirely traverse the slot 232 and cause the push member 262 to deflect upwards into the deflected orientation, whereby the push surface 270 and rear edge 272 can remove, such as by pushing away, biomaterial 9 extending outwardly from the carrier channel 52, thus further preparing the biomaterial 9 for optimum or at least favorable loading within the delivery body 4. The slider body 252 can then be slid in the rearward direction FR until the push member 262 is again located rearward of the slot 232 and in the neutral orientation. Any of the foregoing steps can be repeated as necessary until the carrier channel 52 is loaded with the biomaterial 9 in a desired manner. Additionally, an auxiliary tool, such as the auxiliary tool 136 described above, can be used to manually scrape, push, wipe, and/or tamp biomaterial 9 into the carrier channel 52, or remove excess biomaterial 9 from the carrier channel 52, following operation of the loading device 220 as needed. When the biomaterial 9 is favorably loaded in the carrier channel 52, the carrier 50 can then be removed from the slot 232 and subsequently loaded within the cannulation 12 of the delivery body 4, as described above. After the carrier 50 is removed from the slot 232, a subsequent carrier 50 can be inserted therein and loaded with biomaterial 9 in similar fashion. One advantage of the loading devices described herein is that they are configured for repeated loading of a plurality of carriers 50.

It is also to be appreciated that the tray body 224 can define a plurality of elongate slots 232 for receiving a plurality of carriers 50 to be loaded with biomaterial 9 simultaneously or at least substantially simultaneously. For example, the tray body 224 can include two (2), three (3), four (4), five (5), or more than five (5) slots 232, each for receiving a respective carrier 50 therein. In such embodiments, the tray 222 can be configured to load one or more and up to each of the plurality of carriers 50 simultaneously or at least substantially simultaneously with biomaterial 9, as needed. Moreover, in such embodiments, the floor surface 226 can define a plurality of floor surface portions extending respectively between adjacent slots 232. These floor surface portions can be aligned along a common incline plane, from which the push surface 270 is offset at the back rake angle A4. In such embodiments, the push surface 270 is configured to push biomaterial 9 successively into the slots 232 as the push member 262 moves in the forward direction FD. Additionally, the common incline plane can allow the back rake angle A4 of the push surface 270 to be maintained as the push surface traverses the slots 232 in the forward and rearward directions FD, RD. Additionally, the tray body 224 can also include a respective plurality of access ports 234 and/or carrier retention receptacles 237 in communication with the plurality of slots 232.

Figure 11B:
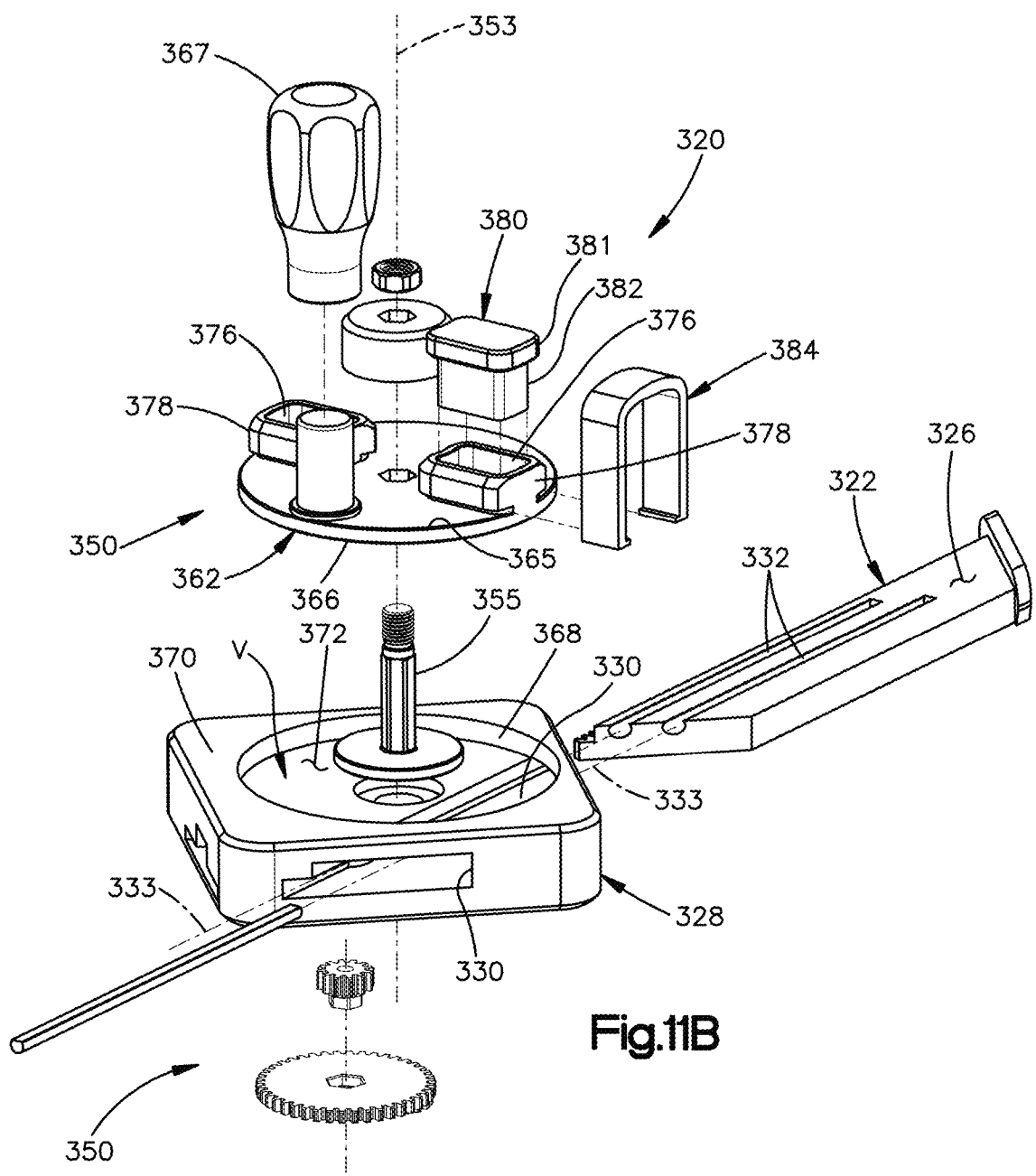
FIG. 11B is an exploded perspective view of the loading device illustrated in FIG. 11A.
Figure 11C:
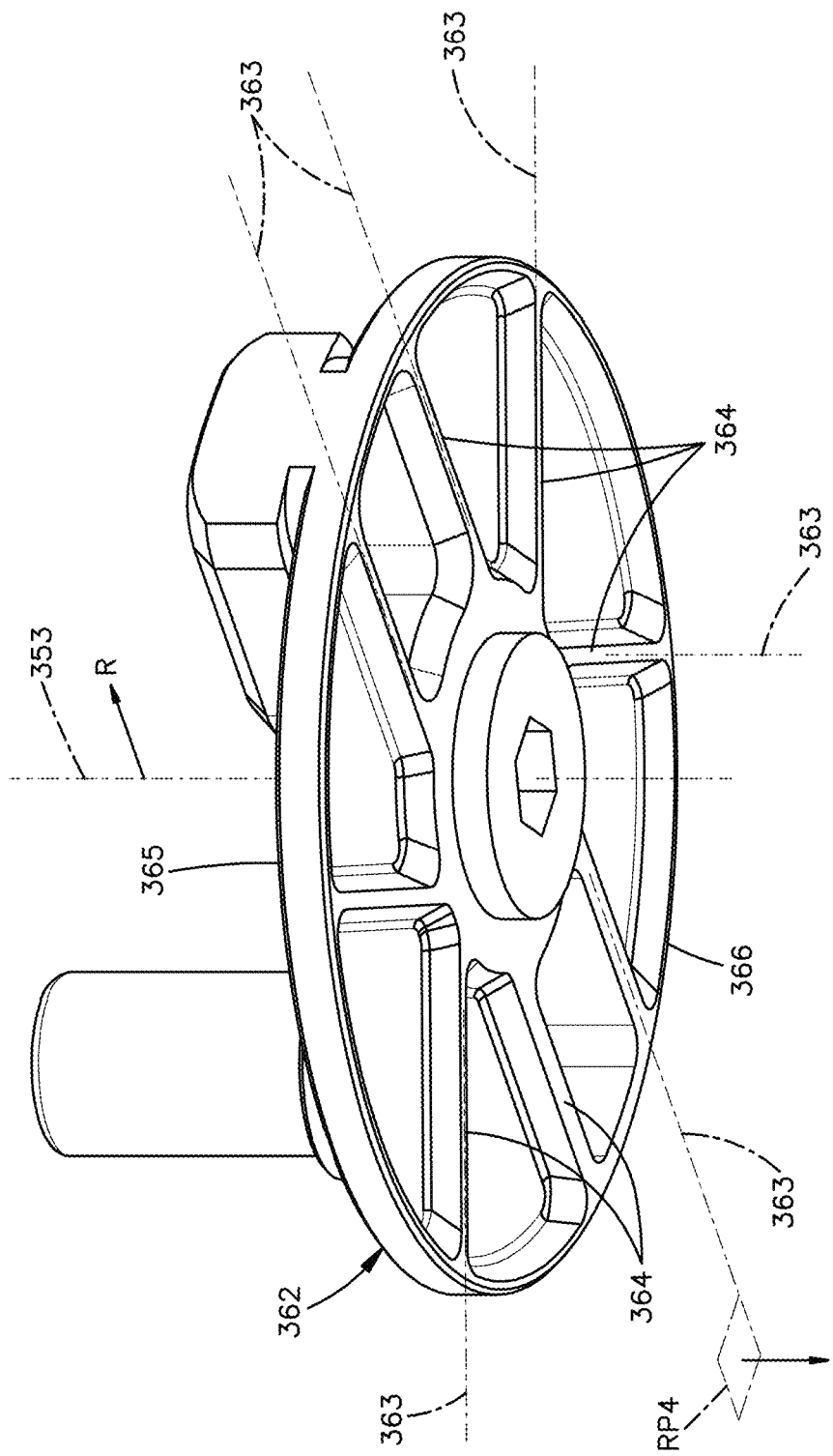
FIG. 11C is a perspective view of an underside of a rotary pusher member of the loading device illustrated in FIG. 11A.

Referring now to FIGS. 11A and 11B, in other embodiments, a loading device 320 can include a tray 322 having one or more slots 332 for receiving the elongate body portions 55 of corresponding one or more carriers 50, and a rotary mechanism 350 for directing biomaterial 9 into the one or more slots 332. The tray 322 comprises a tray body 324 that defines a first or top tray surface 326. The one or more slots 332 are recessed within the tray body 324 from the top tray surface 326 along the vertical direction Z. The loading device 320 includes a housing 328 that at least partially defines an internal volume V configured for receiving biomaterial 9 (FIG. 11B). The housing 328 also defines a tray receptacle 330 that is in communication with the internal volume V and is also configured to receive at least a portion of the tray body 324, particularly the portion thereof defining the one or more slots 332. The housing 328 is configured such that the internal volume V is in communication with the one or more slots 332 when the tray 322 resides in the tray receptacle 330. Thus, the tray 322 can be characterized as an "insert" or "cartridge" configured for insertion within the housing 328 so as to place the one or more slots 332 in communication with the internal volume V. The tray body 324 can define a handle 325 for manipulating the tray 322, such as for inserting the tray 322 within the tray receptacle 330. It is to be appreciated that the tray body 324 can define carrier retention receptacles at distal ends of the slot 332 for retaining the carriers 50 such that the carrier channels 52 remain open to the internal volume V, similarly as described above with reference to other embodiments. It is also to be appreciated that the tray body 324 can include more than two (2) slots 332, including three (3), four (4), five, (5), six (6) seven (7), eight (8), nine (9), ten (10), or more than ten (10) slots 332, for example. The size of the loading device 320, including the size of the tray body 324, can be scaled upward or downward in size as necessary to accommodate as many or as few slots 332 needed for a particular biomaterial-loading application. In multi-slot embodiments, the loading device 320 can include one or more slot inserts 359 (FIG. 11A) for occupying any unused slots 332, thus preventing the biomaterial 9 from filling the unused slots during use of the device.

The rotary mechanism 350 includes a push member, such as a rotary disk 362, that is configured to move biomaterial 9 deposited within the internal volume V into the one or more slots 332 as the rotary disk 362 rotates about an axis of rotation 353. In particular, as shown in FIG. 1C, the rotary disk 362 includes one or more pusher features, such as wipers 364 on an underside 366 of the rotary disk 362 opposite a top surface 365 of the rotary disk 362. The wipers 364 are configured to push biomaterial 9 within the internal volume V across the top surface 326 of the tray body 324 and into the one or more slots 332, as described in more detail below. One or more and up to all of the wipers 364 can be elongate along respective central wiper axes 363 that are linear and extend along a horizontal reference plane RP4 (i.e., a reference plane orthogonal to the vertical direction Z). One or more and up to all of the central wiper axes 363 can be offset from a radial direction R perpendicular to the axis of rotation 353. That is to say, one or more and up to all of the central wiper axes 363 can be skewed from (i.e., not intersect) the axis of rotation 353. Alternatively, one or more and up to all of the central wiper axes 363 can extend along a respective radial direction R that intersects the axis of rotation 353. It is to be appreciated that one or more and up to all of the central wiper axes 363 can be curved in the horizontal reference plane RP4. It should be appreciated that the wiper axes 363 are oriented relative to the slot axes 333 for effective movement of biomaterial 9 into the slots 332.

Referring again to FIG. 11B, the axis of rotation 353 can be centrally defined by a spindle 355. The spindle 355 can be separate from, and coupled to, the rotary disk 362, as shown; although in other embodiments the spindle 355 and the rotary disk 362 can be monolithic with each other. A control member, such as a handle 367, can be coupled to the rotary disk 362 and configured to drive rotation of the rotary disk 362 about the axis of rotation 353. The handle 367 can extend, for example, from the top surface 365 of the rotary disk 362. The housing 328 can define a disk receptacle 368 in which the rotary disk 362 resides. As shown, the disk receptacle 368 can extend downwardly from, and be at least partially defined by, a top surface 370 of the housing 328. The housing 328 can also define a base surface 372 recessed below the top housing surface 370 and defining a base of the disk receptacle 368. The base surface 372 also defines a base surface of the internal volume V. When the tray 322 is inserted within the tray receptacle 330, the top surface 326 of the tray 322 is preferably flush with the base surface 372 and partially defines the internal volume V.

Figure 11D:
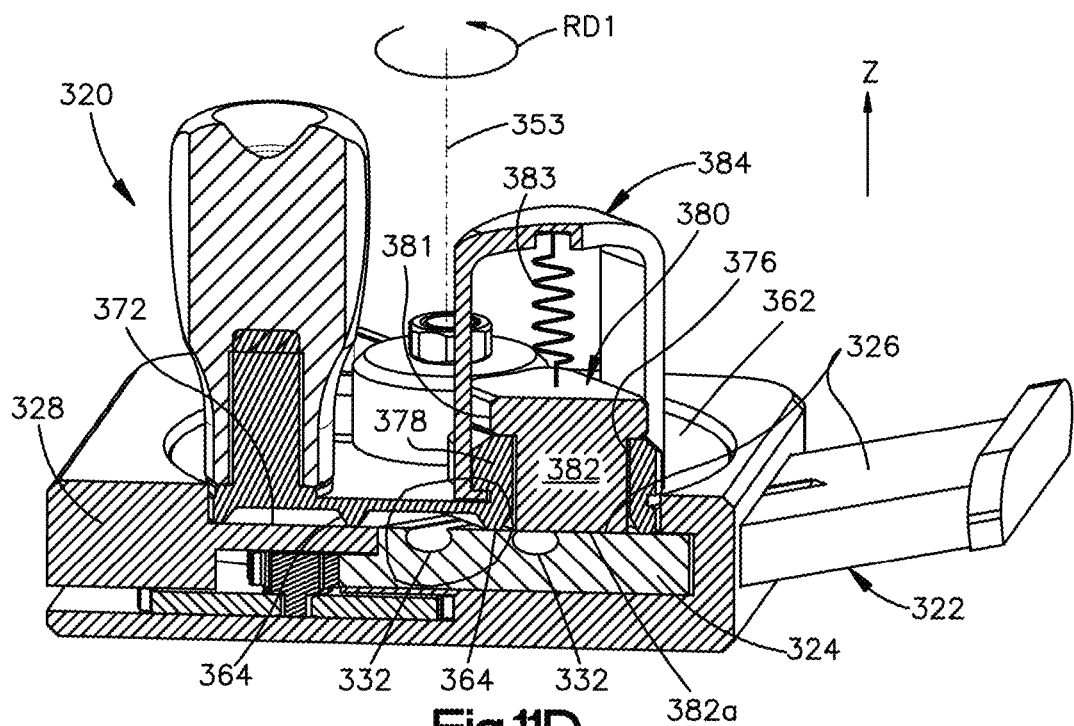
FIG. 11D is a sectional perspective view of the loading device along section line 11D-11D in FIG. 11A.

As best shown in FIGS. 11B and 11D, the loading device 320 can include one or more inlets 376 each providing communication from an exterior of the device 320 into the internal volume V. As shown, the inlets 376 can be defined by the rotary disk 362 and can extend from the top surface 365 to the underside 366 of the disk, particularly a portion of the underside 366 offset from the one or more wipers 364. The inlets 376 can each be at least partially defined by an inlet formation 378 that extends vertically upwards from the top surface 365 of the rotary disk 362. The inlet formation 376 can be characterized as a "hopper" configured to hold biomaterial 9 prior to the biomaterial 9 being directed into the internal volume V. An inlet cap 380 can be configured to cover the inlet 376. The cap 380 can include a handle portion 381 and protrusion 382 extending downwardly from the handle portion 381 and having a complimentary geometry with the inlet 376. The cap 380 can be configured so that the protrusion 382 extends within the inlet 376 for pushing biomaterial 9 into the internal volume V. As shown, the cap 380 can also be configured such that a bottom surface 382a of the protrusion 382 abuts the top surface 326 of the tray body 324 when the handle portion 381 abuts the inlet formation 378. In this manner, the cap 380 can be employed as a tamp member to tamp biomaterial 9 into the one or more slots 332 as needed when the rotary disk 362 positions the cap 380 over the one or more slots 332. A cover 384 can be configured to couple with the inlet formation 378 and cover the cap 380. In additional embodiments, a biasing member, such as a spring 383, can operatively couple the cap 380 to the cover 384, and can be configured to bias the bottom surface 382a of the protrusion 382 against the top surface 326 of the tray body 324 so as to force biomaterial 9 downward into the one or more slots 332 when the cover is coupled with the inlet formation 378. In such embodiments, the cap 380 and cover 384 can be detached from the inlet formation 378 when it is desired to deposit biomaterial 9 within the inlet 376, and can be subsequently coupled to the inlet formation 378 to provide a constant downward force for pushing the deposited biomaterial 9 into the one or more slots 332.

The loading device 320 can include two or more such inlets 376 located on the rotary disk 362 so that a pair of inlets 376 are spaced from each other about the circumference of the rotary disk 362, such as on opposite sides of the axis of rotation 353. In this manner, the rotary disk 362 can be rotated so as to locate one of the inlets 376 over the base surface 372 of the housing 328 and the other inlet 376 over the tray 322, such as over the one or more slots 332 thereof. Such an inlet design provides flexibility in the use and operation of the loading device 320. For example, one of the inlets 376 can be used for depositing biomaterial 9 within the internal volume, while the other inlet 376, particularly the cap 380 thereof, can optionally be used as a tamp for tamping biomaterial 9 within the one or more slots 332. It is to be appreciated that other inlet 376 configurations are within the scope of the present disclosure.

Figure 11E:
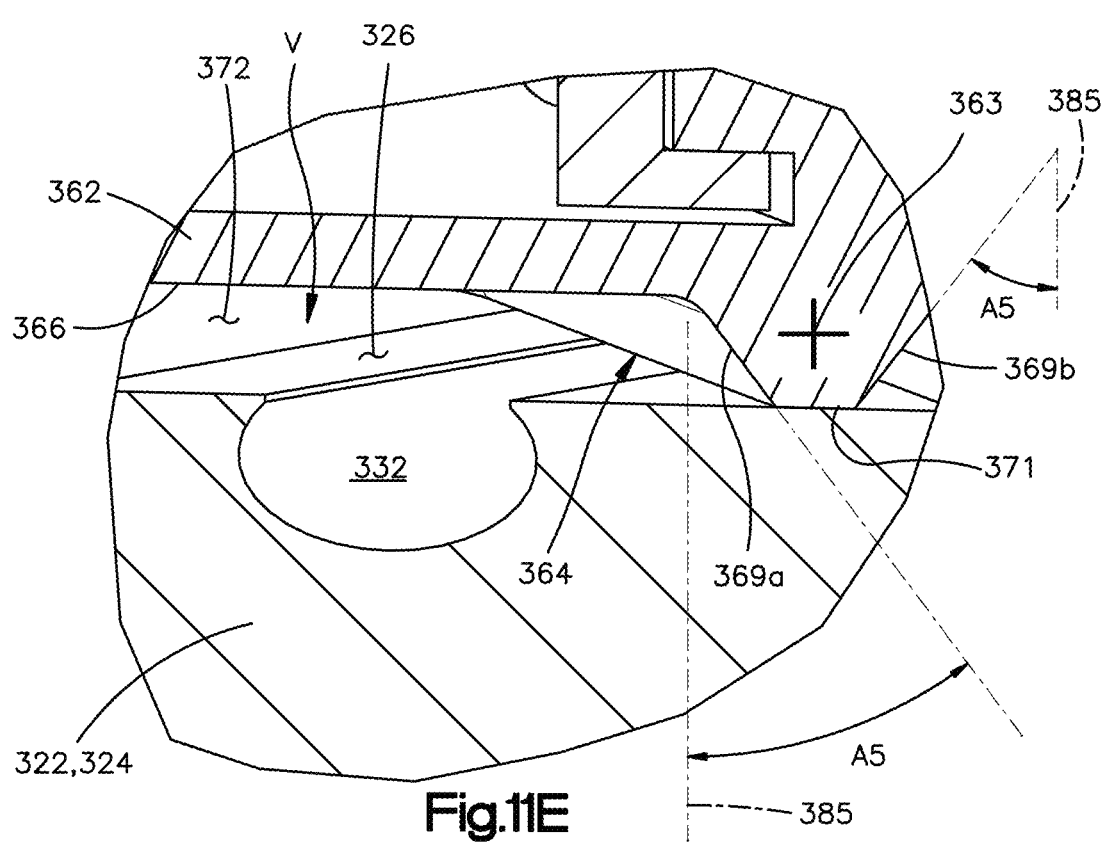
FIG. 11E is an enlarged view of area 11E-11E shown in FIG. 11D.

As shown in FIGS. 11D and 11E, the wipers 364 extend downwardly from the rotary disk 362 and contact, or at least be in close proximity to, the base surface 372 of the housing 328, such that rotation of the rotary disk 362 causes the wipers 364 to move biomaterial 9 across the base surface 372 and/or across the top surface 326 of the tray 322, in one or both of a first rotational direction RD1 and a second rotational direction RD2 about the axis of rotation 353, and into the one or more slots 332. Referring now to FIG. 11E, one or more and up to all of the wipers 364 can have a bottom wiper surface 371, as well as opposed first and second side wiper surfaces 369a, b that extend downwardly from the underside 366 of the rotary disk 362 to the bottom wiper surface 371. One or both of the side wiper surfaces 369a, b can taper inwardly from the underside 366 to the bottom wiper surface 371 at a taper angle A5, as measured with respect to a vertical axis 385 in a reference plane orthogonal to the central wiper axis 363. The taper angle A5 advantageously causes the respective side wiper surface 369a, b to direct the biomaterial 9 downwardly into the one or more slots 322 as the wiper 364 traverses the one or more slots 332. It is to be appreciated that, on one or more and up to all of the wipers 364, the taper angle A5 of the first side wiper surface 369a can be different than that of the second side wiper surface A5. One or more and up to all of the wipers 364 can be comprised of a flexible material having a low hardness, as measured by a durometer, which provides the wiper(s) 364 with flexibility, as described above. One or more and up to all of the wipers 364 can optionally be monolithic with the rotary disk 362. For example, the rotary disk 362 and the wipers 364 can be monolithically formed of a flexible material having a low hardness.

Referring now to FIG. 11F, the rotary mechanism 350 can comprise an actuation assembly, such as a gear assembly 386, for translating the tray 322 along a forward direction FD relative to the housing 328 as the rotary disk 362 rotates about the axis 353 along the first rotational direction RD1, and also along a rearward direction RD as the rotary disk 362 rotates about the 353 along the second rotational direction RD2. The gear assembly 386 is configured such that the wipers 364 will move substantially against the direction FD, RD at which the tray body 324 moves, regardless of whether the rotary disk 362 rotates in the first or second rotational direction RD1, RD2. In this manner, the rotary disk 362 can be rotated back and forth in the first and second rotational directions RD1, RD2 as needed until the biomaterial 9 is satisfactorily loaded into the channels 52 of the one or more carriers 50. The gear assembly 386 can include a spindle gear 388 that rotates with the spindle 355 and drives a pinion 390, which, in turn, is configured to drive a rack 392 defined by, or carried by, the tray body 324. In this manner, the loading device 320 can translate the tray 322, along with any carriers 50 inserted therein, through the internal volume V and beneath the wipers 364, so as to deposit biomaterial 9 into the carrier channels 52. As shown, the gear assembly 386 can also include an intermediate gear 394 having teeth 395 that intermesh with teeth 389 of the spindle gear 388. The pinion 390 can extend from, and have a gear axis 397 common with, the intermediate gear 394. The pinion 390 has teeth 391 that intermesh with teeth 393 of the rack 392. The gear assembly 386 can employ a gear ratio that is selected for maximizing loading of the biomaterial 9 within the one or more carrier channels 52. It is to be appreciated that the gear assembly 386 can employ gear configurations different than that shown in the present embodiment.

Referring now to FIG. 12A, a loading device 410 can include a housing 422 that includes one or more slots 432 for receiving corresponding one or more carriers 50, and a rotary mechanism 450 for directing biomaterial 9 into the one or more slots 432. In the present embodiment, the rotary mechanism 450 includes a first rotary member, such as an auger 452, that is configured to move biomaterial 9 deposited within the housing 422 into the one or more slots 432. The rotary mechanism 450 can also include a second rotary member, such as a drive member 470 that is configured to drive rotation of the auger 452 relative to the housing 422. The housing 422 includes a housing body 424 having a drum-like configuration configured to receive the auger 452 and the drive member 470, such that the loading device 410 defines an internal volume V of space between the housing body 424 and the auger 452.

The housing body 424 has an inner surface 426 and an outer surface 428 opposite the inner surface 426. The inner surface 426 defines an opening or chamber 430 of the housing 422, such that a central axis 453 of the rotary mechanism 450 extends centrally through the chamber 430. The housing 422 can include a central post 434 that extends along the central axis 453. The chamber 430 is configured to house the auger 452 and the drive member 470. The auger 452 defines an outer surface 454 configured to face the inner surface 426 of the housing body 424 in a manner defining the internal volume V annularly therebetween. The auger 452 includes at least one member, such as external threads 456 extending helically along the outer surface 454, configured to move a quantity of the biomaterial 9 from within the internal volume V into one or more slots 432, particularly into carrier channels 52 inserted within the one or more slots 432, responsive to rotation of the auger 452 relative to the housing body 424. The external thread 456 can be a single-lead, continuous thread 456 extending helically along the outer surface 454, although in other embodiments the external thread 456 can include a plurality of thread segments, such as double- or triple-lead thread segments, and/or one or more discontinuous thread segments. The external threads 456 can be comprised of a flexible material having a low hardness, such as rubber, silicone, or the like, by way of a non-limiting examples. In this manner, the external threads 456 can possess a level of flexibility, which, as described above, is advantageous for moving or "wiping" biomaterial 9 into the slots 432. Furthermore, the auger 452 can optionally be a monolithic body that defines the external thread 456. In such embodiments, the auger 452, and thus the external thread 456 thereof, can be comprised of the flexible material. The auger 452 can also define an inner surface 458 opposite the outer surface 454 and configured to house the drive member 470. The drive member 470 defines an outer surface 472 that can be configured to face and reside within the inner surface 458 of the auger 452. In this manner, the drive member 470 can be configured to nest within the auger 452, which is configured to nest within the housing body 424.

It is to be appreciated that the drive member 470 is configured to engage the auger 452, such as via complimentary engagement features, in a manner such that rotation of the drive member 470 about the central axis 453 also rotates the auger 452 about the central axis 453. For example, the auger 452 and the drive member 470 can be coupled together, such as by press-fitting, heat shrinking, adhesives, and/or mechanical fasteners and the like. The drive member 470 can also define an inner surface 474 opposite the outer surface 472. The inner surface 426 of the housing body 424 and the outer surface 454 of the auger 452 preferably have complimentary inverted frusto-conical shapes about the central axis 453. The inner surface 458 of the auger 452 and the outer surface 472 of the drive member 470 can also have complimentary inverted frusto-conical shapes about the central axis 453. The inner surface 474 of the drive member 470 can also have an inverted frusto-conical shape. The outer surface 428 of the housing body 424 can also have an inverted frusto-conical shape. In other embodiments, however, the inner surface 426 of the housing body 424 and the outer surface 454 of the auger 452 can have complimentary cylindrical shapes.

The inner surface 474 of the drive member 470 defines a drive member chamber 476. The drive member 470 defines a drive coupling 478, which can be a post centrally located within the drive member chamber 476 and extending along the central axis 453. The drive coupling 478 can have one or more formations for transmitting a rotational drive force to the drive member 470 and thus also to the auger 452. One such formation can include knurls or teeth 480 on an exterior of the drive coupling 478. The teeth 480 can provide grip facilitating manual rotation of the drive member 470 about the central axis 453. Accordingly, the drive coupling 478 can also be referred to as a "rotary handle". The teeth 480 can also be configured to intermesh with one or more complimentary teeth of a drive tool. Another such formation can include a socket 482 extending downwardly from an upper end of the drive coupling and configured to receive a complimentary drive tool, such as a drive bit of a manual driver or a powered driver, by way of non-limiting examples. It is to be appreciated that other types and configurations of the drive coupling 478 are within the scope of the present disclosure for driving rotation of the drive member 470.

Referring now to FIG. 12B, the central post 434 can extend upwardly along the vertical direction Z from a base surface 436 of the housing body 424. The base surface 436 defines a bottom end of the chamber 430. The base surface 436, as well as the inner surface 426, are configured for receiving the biomaterial 9 within the internal volume V, as described in more detail below. The housing body 424 defines the one or more slots 432, which are recessed radially outward from the inner surface 426 with respect to the central axis 453 and are in communication with the internal volume V. Thus, the one or more slots 432 can be characterized as being defined within the inner surface 426. The one or more slots 432 each extend along a respective slot axis 433. As shown, the housing body 424 preferably has a plurality of slots 432, which can be spaced equidistantly about the circumference of the inner surface 426. The one or more slots 432 are each configured such that the elongate body portions 55 of the carriers 50 can be inserted within the slot 432 along the central slot axis 433. The one or more slots 432 and the carrier 50 are cooperatively configured such that the central axis 10 of the carrier 50 is substantially coincident with the central slot axis 433. The one or more slots 432 can extend to, and be at least partially defined by, the base surface 436. The housing body 424 can define carrier retention receptacles at distal ends of the slot 432 for retaining the carriers 50 therein such that the carrier channels 52 remain open to the internal volume V, similarly as described above with reference to other embodiments.

In the illustrated embodiment, the housing body 424 defines five (5) slots 432; however in other embodiments the housing body 424 can define more than five slots (5) slots 432, such as six (6), seven (7), eight (8), nine (9), ten (10), or more than ten (10) slots 432. The housing body 424 can also define less than five slots, such as four (4), three (3), or two (2) slots 432 or one (1) single slot 432. It is to be appreciated that the circumference of the housing body 424 can be scaled upward or downward in size as necessary to accommodate as many slots 432 as needed for a particular biomaterial-loading application.

Figure 12A:
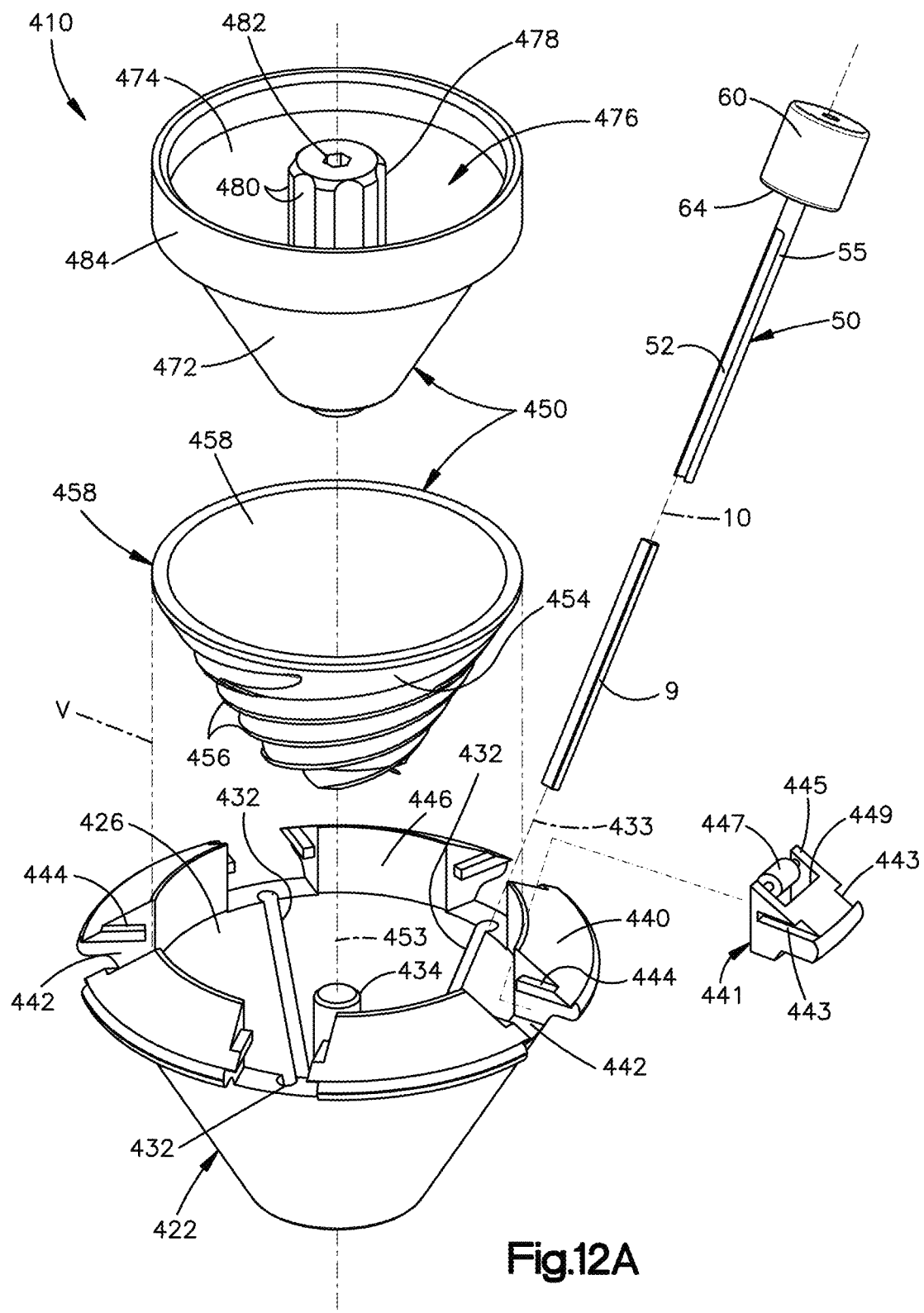
FIG. 12A is an exploded perspective view of yet another example of a loading device for loading flowable biomaterial into the carrier of the instrument assembly illustrated in FIG. 1A, according to another embodiment of the present disclosure.
Figure 12D:
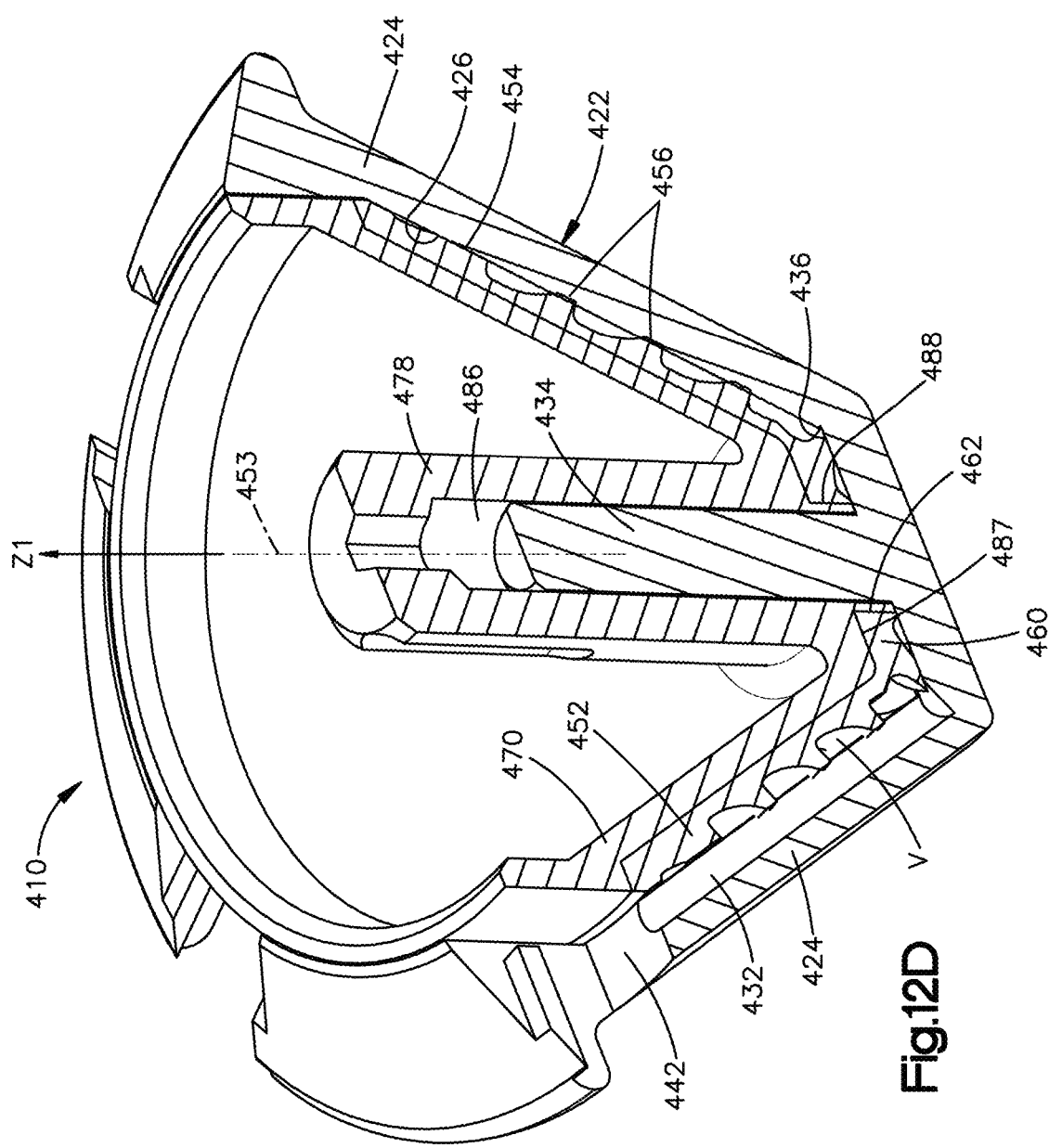
FIG. 12D is a sectional perspective view of the loading device illustrated in FIG. 12C.

Referring again to FIG. 12A, the housing 422 can also define a rim structure 440 for receiving the stop members 60 of the carriers 50. The rim structure 440 can define one or more respective rim openings 442 for receiving an insert 441. The rim structure 440 can include rails or platforms 444 located in the rim openings 442 for engaging complimentary slots 443 defined in the sides of the inserts 441. Thus, the inserts 441 can be said to fit within the associated rim openings 442 in "dovetail" fashion. The insert 441 can have a support surface 445 for supporting the distal surfaces 64 of the stop members 60. The insert 441 can also include a tamp member, such as a roller 447, which can be received within an insert opening 449 defined by the insert 441. The insert 441 is configured such that, when it resides within the associated rim opening 442, the elongate body portion 55 of the carrier 50 can be inserted into and withdrawn from the slot 432 through the insert opening 449. The roller 447 is configured to engage the edges of the elongate channel opening 53, whereby the roller 447 can tamp or press the biomaterial 9 loaded within the channel 52 as the carrier 50 is withdrawn, thereby also removing any excess material 9 from the carrier 50. The roller 447 is preferably comprised of a flexible material having a low hardness, such as those materials described above. The rim structure 440 can also define an inner rim surface 446 that has a substantially cylindrical configuration. The inner rim surface 446 can be configured to interface with an outer cylindrical surface 484 of the drive member 470, such as to cooperatively provide the loading device 410 with a supplemental journal bearing mechanism. The outer cylindrical surface 484 of the drive member 470 can also engage inner surfaces of the inserts 441 so as to retain the inserts 441 within the rim openings 442 during operation of the loading device 410. Although a single insert 441 is shown in FIG. 12A, it should be appreciated that the loading device 410 can include a plurality of inserts 441, including an insert 441 for each of the rim openings 442.

The rotary mechanism 450 can be configured for quick and repeated detachment from and re-attachment with the housing 424. For example, the auger 452 and the drive member 470, coupled together as described above, can rest freely in the chamber 430 of the housing body 424, and can be configured to be lifted together manually by gripping the rotary handle 478 and lifting upward. With the rotary mechanism 450 detached, biomaterial 9 can be deposited in the chamber 430, such as on the base surface 436, and the rotary mechanism 450 can be re-attached to the housing body 424, such as by inserting the rotary handle 478 over the central post 434 of the housing body 424. From this re-attached position, the rotary handle 478 can be manually rotated (or rotated under power), thereby driving the external thread 456 about the central axis 453, in turn causing the thread 456 to move the biomaterial 9 upwardly along the inner surface 426 of the housing body 424. In this manner, the external thread 456 moves the biomaterial 9 from the internal volume V and into one or more carrier channels 52 disposed respectively within the one or more slots 432.

Referring now to FIG. 12D, the external thread 456 can define a crest that can abut, or at least be in close proximity to, the inner surface 426 as well as the base surface 436, and can thus be configured to scrape, wipe, push, or otherwise direct biomaterial 9 from the internal volume V into the one or more slots 432. In the illustrated embodiment, the loading device 410 defines a direction of axial advancement Z1 that is oriented along the central axis 453 and upward along the vertical direction Z. Thus, the depicted loading device 410 is configured to move the deposited biomaterial 9 away from the base surface 436 and upwardly along the inner surface 426 and into the one or more slots 432. It is to be appreciated, however, that in other embodiments, the direction of axial advancement Z1 can be downward in the vertical direction Z, whereby the loading device 410 can be configured to move biomaterial 9 from a base surface at or near a top of the housing 422 and downward along the inner surface 426 and into the one or more slots 432. Other configurations are also within the scope of the present disclosure.

The central post 434 of the housing 422 can extend within a central bore 486 of the drive member 470. Additionally, the auger 452 can include a base portion 460 at a bottom end thereof that interfaces with the base surface 436 of the housing body 424. The base portion 460 of the auger 452 can define a central base aperture 462 through which the central post 436 of the housing body 424 extends. The drive member 470 can define a base portion 487 at the bottom end thereof that interfaces with the base portion 460 of the auger 452. The drive member 470 can also define a mounting structure, such as a bushing 488, that extends through the central base aperture 462 of the auger 452 and can extend to, and interface with, the base surface 436 of the housing body 424.

Although the disclosure has been described in detail, it should be understood that various changes, substitutions, and alterations can be made herein without departing from the spirit and scope of the invention as defined by the appended claims. For example, features of the various embodiments described herein can be incorporated into one or more and up to all of the other embodiments described herein. Moreover, the scope of the present disclosure is not intended to be limited to the particular embodiments described in the specification. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. A system for delivering flowable biomaterial into an intervertebral disc space between an upper vertebral body and a lower vertebral body of a patient, the system comprising:
    a plurality of delivery bodies each configured for delivering the biomaterial, each of the plurality of delivery bodies defining:
        a proximal end, an elongate outer surface extending from the proximal end to a distal end spaced from the proximal end along a longitudinal direction, a mounting formation at the proximal end, the mounting formation configured to couple with a handle member, a cannulation opposite the outer surface along a radial direction, the cannulation extending from the proximal end to at least one opening adjacent the distal end;
        a distal region including a tip that extends to the distal end, the distal region defining a maximum height at a location proximally spaced from the distal end, the maximum height measured along a second direction perpendicular to the longitudinal direction,
            wherein the maximum heights of at least some of the distal regions of the plurality of delivery bodies are different from one another, and the distal regions are configured to provide feedback indicating a distance between the upper and lower vertebral bodies along a cranial-caudal direction;
    a carrier that defines a channel elongate along the longitudinal direction, the carrier configured for insertion within the cannulation from the proximal end of any of the plurality of delivery bodies to carry the biomaterial within the cannulation; and
    an advancement member configured for insertion within the cannulation of any of the plurality of delivery bodies so as to forcibly advance the biomaterial from the cannulation, through the at least one opening, and into the interverbal disc space.

2. The system of claim 1, wherein the distal region defines a first contact surface and a second contact surface opposite each other along the second direction, the maximum height is defined between the first and second contact surfaces, and the first and second contact surfaces are configured to contact opposed endplates of the first and second vertebral bodies, respectively.

3. The system of claim 2, wherein the first and second contact surfaces each have a substantially linear profile in a reference plane orthogonal to a central axis of the respective delivery body.

4. The system of claim 2, wherein the tip defines tapered surfaces extending from the location to the distal end, and the tapered surfaces are configured to expand the distance between the first and second vertebral bodies along the cranial-caudal direction as the delivery body advances distally into the intervertebral disc space.

5. The system of claim 1, wherein the at least one opening includes a pair of opposed side openings spaced from each other along a third direction perpendicular to the longitudinal and second directions.

6. The system of claim 5, wherein at least one of the delivery bodies includes a wedge formation at a distal terminal end of the cannulation, and the wedge formation faces proximally and intersects a central axis of the cannulation, whereby the wedge formation is configured to divert the biomaterial from the cannulation out the pair of opposed side openings.

7. The system of claim 5, wherein the at least one opening includes a third opening at the distal end, wherein a central axis of the at least one of the delivery bodies extends through the third opening.

8. The system of claim 1, wherein the at least one opening is a single opening that is open at least along a third direction perpendicular to the longitudinal and second directions.

9. The system of claim 1, wherein the at least one opening of at least one of the plurality of delivery bodies is located at the distal end such that a central axis of the at least one of the delivery bodies extends through the at least one opening.

10. A system for delivering flowable biomaterial into an intervertebral disc space between an upper vertebral body and a lower vertebral body of a patient, the system comprising:
    a plurality of delivery bodies each configured for delivering the biomaterial, each of the plurality of delivery bodies defining:
        a proximal end, a distal end spaced from the proximal end along a longitudinal direction, a cannulation extending from the proximal end to at least one opening adjacent the distal end,
        a distal region including a tip that extends to the distal end, the distal region defining a maximum height at a location proximally spaced from the distal end, the maximum height measured along a second direction perpendicular to the longitudinal direction, wherein the maximum heights of at least some of the distal regions of the plurality of delivery bodies are different from one another, and the distal regions are configured to provide feedback indicating a distance between the upper and lower vertebral bodies along a cranial-caudal direction;

a carrier that defines a channel elongate along the longitudinal direction, the carrier configured for insertion within the cannulation of any of the plurality of delivery bodies to carry the biomaterial within the cannulation; and an advancement member configured for insertion within the cannulation of any of the plurality of delivery bodies so as to forcibly advance the biomaterial from the cannulation, through the at least one opening, and into the interverbal disc space, wherein:

the at least one opening of at least one of the plurality of delivery bodies is located at the distal end such that a central axis of the at least one of the delivery bodies extends through the at least one opening, at least one of the plurality of delivery bodies defines an interior surface that defines the cannulation, the interior surface defines helical threads extending along a distal portion of the cannulation that extends to the distal end, the advancement member defines a complimentary distal member portion that defines a pair of opposed surfaces that are substantially planar and spaced from each other along a direction perpendicular to a central axis of the at least one of the plurality of delivery bodies, and the at least one of the plurality of delivery bodies is rotatably connectable to the advancement member about the central axis, whereby the at least one delivery body and the advancement member are cooperatively configured such that rotation of the helical threads relative to the pair of opposed surfaces about the central axis advances the biomaterial distally through the cannulation and out the at least one opening and into the intervertebral disc space.

* * * * *